United States Patent
Winum et al.

(10) Patent No.: US 8,372,871 B2
(45) Date of Patent: Feb. 12, 2013

(54) HISTIDINOL DEHYDROGENASE INHIBITORS, AND USE THEREOF AS MEDICAMENTS

(75) Inventors: Jean-Yves Winum, Saint Andre de Sangonis (FR); Jean-Louis Montero, Lauret (FR); Stephan Köhler, Saint Clement de Riviere (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/128,886

(22) PCT Filed: Nov. 10, 2009

(86) PCT No.: PCT/FR2009/052159
§ 371 (c)(1),
(2), (4) Date: Sep. 19, 2011

(87) PCT Pub. No.: WO2010/055254
PCT Pub. Date: May 20, 2010

(65) Prior Publication Data
US 2012/0129907 A1    May 24, 2012

(30) Foreign Application Priority Data
Nov. 12, 2008   (FR) ..................... 08 06286

(51) Int. Cl.
*A61K 31/417* (2006.01)
*A61K 31/42* (2006.01)
*A61K 31/422* (2006.01)
*A61K 31/426* (2006.01)
*A61K 31/427* (2006.01)

(52) U.S. Cl. ..... 514/365; 548/203; 548/236; 548/311.1; 548/335.5; 514/374; 514/396; 514/397

(58) Field of Classification Search .................. 514/365, 514/374, 396, 397; 548/203, 236, 311.1, 548/335.5
See application file for complete search history.

(56) References Cited

PUBLICATIONS

Pascale, Joseph et al, "Targeting of the Crucells Suis Virulence Factor Hisidinol Dehydrogenase by Histidinol Analogues Results in Inhibition of Intramacrophagic Multiplication of the Pathogen," Antimicrobial Agents and Chemotherapy, 2007, vol. 51 (10), pp. 3752-3755.*

Joseph, Pascale et al: "Targeting of the *Brucella suis* virulence factor histidinol dehydrogenase by histidinol analogues results in inhibition of intramacrophagic multiplication of the pathogen", Antimicrobial Agents and Chemotherapy, 2007, 51(10), 3752-3755, XP002518058.

Abdo, Marie-Rose et al: "*Brucella suis* histidinol dehydrogenase: Synthesis and inhibition studies of a series of substituted benzylic ketones derived from histidine", Bioorganic &Medicinal Chemistry, 2007, 15(13), 4427-4433, XP022093284.

Dancer, Jane E. et al: "Synthesis of potent inhibitors of histidinol dehydrogenase", Bioorganic & Medicinal Chemistry Letters, 1996, 6(17), 2131-2136, XP004135671.

French Search Report, dated Mar. 6, 2000, in FR 0806286.

* cited by examiner

*Primary Examiner* — Kamal Saeed
*Assistant Examiner* — Janet L Coppins
(74) *Attorney, Agent, or Firm* — Young & Thompson

(57) ABSTRACT

Compounds of general formula (I) below:

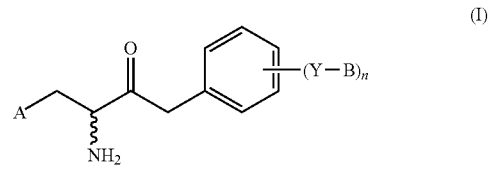

(I)

are characterized in that
A represents in particular a $C_5$-$C_{10}$ heterocyclic group,
Y represents in particular a single bond, and
B represents in particular an aryl or heteroaryl group.

15 Claims, 1 Drawing Sheet

**Intracellular proliferation of *Brucella suis***

HISTIDINOL DEHYDROGENASE INHIBITORS, AND USE THEREOF AS MEDICAMENTS

A subject of the present invention is histidinol dehydrogenase inhibitors. The present invention also relates to the use of these histidinol dehydrogenase inhibitors as medicaments.

Brucellosis, also called Maltese fever, rock fever, undulant fever, melitococcosis or Mediterranean fever is an anthropozoonosis (disease transmitted to humans by animals) caused by coccobacilli of the genus *Brucella*.

Although human brucellosis has become rare in France since stringent prophylactic measures were introduced in 1978, it remains a disease which can result in serious complications if treatment is not implemented rapidly. As for any infectious disease, the prevention (monitoring and eradication of the disease in livestock) remains the best means of control.

The bacteria of the genus *Brucella* are small gram-negative coccobacilli, which are non-encapsulated, non-sporulated and strictly aerobic.

The mechanism of *Brucella*'s pathogenicity still remains unknown. The bacterium is phagocytized by macrophages and develops in the phagosome by inhibiting the fusion of the latter with the lysosomes. The bacterium can thus evade the immune system and maintain the chronicity of the disease.

Moreover, the bacterium synthesizes so-called "septic shock" proteins responsible for the acute phase of the disease.

In humans, certain species of *Brucella* cause a generalized infection with septic state; subsequent visceral or osteoarticular localizations are possible. The disease generally passes through an acute phase during which the bacteria can be detected in the blood. There is also a strong tendency to pass to chronicity, the bacteria being accommodated in the reticulo-endothelial system (liver, spleen, bone marrow, ganglions) where their intracellular position in the macrophages protects them from the immune system and from treatments [Franco et al., *Lancet Infect Dis* 7 (2007): 775-786].

To date there is no effective vaccine against brucellosis in humans.

Brucellosis is therefore treated with antibiotics. It is important to implement rapid treatment in order to avoid a chronic infection. As *Brucella* is an intracellular bacterium, it is necessary to use antibiotics which are both active on the bacterium and capable of crossing the plasmic membrane barrier of the macrophages. The tetracyclines and rifampicin are often combined with streptomycin, chloramphenicol and the sulphamides in order to treat the disease.

As in many bacterial infections treated with multi-antibiotic therapies, examples of *Brucella*'s resistance to antibiotics have been demonstrated in humans [Baikam et al., *Int. J. Antimicrob. Agents* 23 (2004): 405-407; Kinsara et al., *Antimicrob. Agents Chemother.* 43 (1999): 1531; Memish et al., *J. Infect.* 40 (2000): 59-63]. This spontaneous resistance capacity, as well as the very high degree of infectivity by aerosols, has led specialists to consider *Brucella* as a potential bioterrorism agent and antibiotic-resistant strains can be easily constructed.

Thus, it is important to develop novel molecules making it possible to eradicate the bacteria when they are resistant to the antibiotics conventionally used.

Several teams have studied the "virulome" of *Brucella* in order to identify the factors involved in the pathogenicity of the bacterium [Köhler et al., *Proc. Natl. Acad. Sci. USA* 99 (2002): 15711-15716; Delrue et al., *FEMS Microbiol. Lett.* 231 (2004): 1-12].

Among the factors discovered, the enzyme histidinol dehydrogenase (HDH, EC. 1.1.1.23) has been shown to be essential for the growth of the bacterium in the intracellular state, and therefore of its infectivity. HDH, the last enzyme of the histidine biosynthesis pathway, is found in bacteria, plants and lower eucaryotes such as yeasts, but up to now has not been found expressed in mammals [Nagai et al., *Proc. Natl. Acad.* 88 (1991): 4133-4137].

Due to the absence of its equivalent in mammals, HDH constitutes a therapeutic target for the development of anti-infectious treatments against pathogens with histidine-dependent intracellular development.

Several molecules aimed at inhibiting the activity of this enzyme have been developed and are described in the prior art.

Abdo et al. [Abdo et al. *Bioorg Med Chem* 15 (2007): 4427-4433] have described benzyl ketone derivatives of histidine, which are capable of inhibiting histidinol dehydrogenase in vitro.

Abdo et al. [Abdo et al. *J Enzyme Inhib Med Chem* 23 (2008): 357-361] have also described phenyl sulphonyl hydrazine derivatives of histidine, which are capable of inhibiting histidinol dehydrogenase in vitro.

Joseph et al. [Joseph et al. *Antimicrob Agents Chemother* 51 (2007): 3752-3755] have shown that the benzyl ketone derivatives of histidine inhibiting histidinol dehydrogenase in vitro, inhibit the proliferation of the bacteria in liquid medium. The authors of this document have also shown that the benzyl ketone derivatives of histidine are capable of reducing the proliferation of the bacteria when they have entered the macrophage. However, among all the inhibitors described in this document, only the benzyl ketone derivatives of histidine having a high affinity for the enzyme exert a strong inhibitory effect on the proliferation of the bacteria in the macrophage.

Thus, there is a real need to provide novel molecules which are capable at a low dose of inhibiting histidinol dehydrogenase, and effectively inhibiting the proliferation of the bacteria in the macrophage.

The Inventors have unexpectedly discovered that the molecules of general formula (I) mentioned below inhibit histidinol dehydrogenase in vitro and in vivo.

A purpose of the invention is to provide novel molecules inhibiting histidinol dehydrogenase.

Another purpose of the invention is to provide medicaments capable of eradicating the bacteria having infected the macrophage.

A subject of the invention is compounds of general formula (I) below:

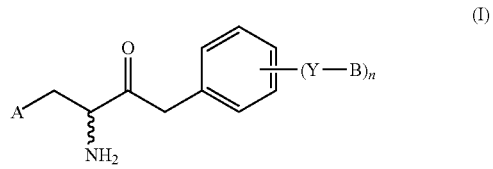

characterized in that
A represents a $C_5$-$C_{10}$, preferentially $C_5$-$C_6$, heterocyclic group comprising 1 to 6 heteroatoms chosen from the elements of the chalcogen and pnictogen families, and the phenyl group is substituted by n Y—B group(s), n varying from 1 to 5, said Y—B group being such that:

Y represents a single bond or a saturated or unsaturated, linear or branched alkylene group, comprising from 1 to 6 carbon atoms, preferably from 2 to 4 carbon atoms, and B represents a group chosen from:
- an aryl or heteroaryl group, in particular a phenyl or naphthyl group
- an A group as defined above, and
- a $C_3$-$C_6$ cycloalkyl group, said B group being optionally substituted by one or more substituent(s), preferentially by one substituent, said substituent(s) being chosen from the group comprising:
- a hydrogen atom,
- a halogen atom,
- an alkoxy group comprising from 1 to 4 carbon atoms,
- an aryloxy group, in particular a phenyloxy group
- a saturated or unsaturated, linear, branched or cyclic alkyl group, comprising from 1 to 6 carbon atoms, preferably from 2 to 4 carbon atoms, optionally substituted by one or more halogen atoms, and
- an aryl group, preferentially a phenyl group, optionally substituted by a $C_1$-$C_4$ alkyl,
- a hydroxyl group,
- a thiol group,
- an amine group,
- an amide group,
- a carboxylic acid group, and
- a cyano group,
- an azide group,
- a nitro group, said compounds being in the form of a racemate, of any one of their enantiomers, or any one of the different tautomers corresponding to said racemates and enantiomers, as well as in the form of their pharmaceutically acceptable salts.

Within the context of the invention, "a $C_5$-$C_{10}$ heterocyclic group" corresponds to any carbon ring comprising a skeleton of 5, or 6 or 7, or 8, or 9 or 10 carbon atoms. In said ring, one or more carbon atoms may be substituted by other atoms different from carbon, and preferentially by an atom of the chalcogen or pnictogen families.

The chalcogen family comprises oxygen (O), sulphur (S), selenium (Se), tellurium (Te), radioactive polonium (Po) and a synthetic element, ununhexium (Uuh). Preferentially, oxygen, sulphur and selenium are chosen as substituent atoms.

The pnictogen family comprises nitrogen (N), phosphorus (P), arsenic (As), the (Sb), bismuth (Bi) and ununpentium (Uup). Preferentially, nitrogen and phosphorus are chosen as substituent atoms.

Said heterocycles of the invention are preferentially $C_5$-$C_6$, i.e. they have a basic skeleton of 5 or 6 atoms.

These heterocycles can be saturated or unsaturated, and thus comprise from no double bonds to 3 double bonds.

The preferred heterocycles of the invention are unsaturated $C_5$-$C_6$ heterocycles chosen from pyrrolidine, tetrahydrothiophene, tetrahydrofuran, piperidine, pyrane, dioxane, morpholine, pyrole, thiophene, furane, pyridine, pyrimidine, pyrazine, triazine, imidazole, thiazole and oxazole, purine, triazole, tetrazole, thiadiazole, and benzothiazole.

Within the context of the invention, Y, when it represents a saturated linear or branched alkylene group, can be chosen from the group comprising: methylene (—CH$_2$—), ethylene (—CH$_2$—CH$_2$—), propylene (—CH$_2$—CH$_2$—CH$_2$—), 1-methylethylene (—CH$_2$(CH$_3$)—CH$_2$—), 2-methylethylene (—CH$_2$—CH$_2$(CH$_3$)—), 1,1-dimethylmethylene (—C(CH$_3$)$_2$—), butylene (—CH$_2$—CH$_2$—CH$_2$—CH$_2$—), 1-methylpropylene (—CH(CH$_3$)—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), 1,2-dimethylethylene (—CH(CH$_3$)—CH(CH$_3$)—), 1,1-dimethylethylene (—C(CH$_3$)$_2$—CH$_2$—), 2,2-dimethylethylene (—CH$_2$—C(CH$_3$)$_2$—), 1-ethylethylene (—CH(C$_2$H$_5$)—CH$_2$—), 2-ethylethylene (—CH$_2$—CH(C$_2$H$_5$)—), 1-ethyl 1-methylmethylene (—C(C$_2$H$_5$)(CH$_3$)—), pentylene (—CH$_2$—CH$_2$—CH$_2$—CH$_2$—CH$_2$—), 1-methylbutylene (—CH(CH$_3$)—CH$_2$—CH$_2$—CH$_2$), 2-methylbutylene (—CH$_2$—CH(CH$_3$)—CH$_2$—CH$_2$), 3-methylbutylene (—CH$_2$—CH$_2$—CH(CH$_3$)—CH$_2$), 4-methylbutylene (—CH$_2$—CH$_2$—CH$_2$—CH(CH$_3$)—), 1,1-dimethylpropylene (—C(CH$_3$)$_2$—CH$_2$—CH$_2$—), 2,2-dimethylpropylene (—CH$_2$—C(CH$_3$)$_2$—CH$_2$—), 3,3-dimethylpropylene (—CH$_2$—CH$_2$—C(CH$_3$)$_2$—), 1,2-dimethylpropylene (—CH(CH$_3$)—CH(CH$_3$)—CH$_2$—), 1,3-dimethylpropylene (—CH(CH$_3$)—CH$_2$—CH(CH$_3$)—), 2,3-dimethylpropylene (—CH$_2$—CH(CH$_3$)—CH(CH$_3$)—), 1,1,2-trimethylethylene (—C(CH$_3$)$_2$—CH(CH$_3$)—), 1,2,2-trimethylethylene (—CH(CH$_3$)—C(CH$_3$)$_2$—), hexylene (—CH$_2$—CH$_2$—CH$_2$—CH$_2$—CH$_2$—CH$_2$—), 1-methylpentylene (—CH(CH$_3$)—CH$_2$—CH$_2$—CH$_2$—CH$_2$—), 2-methylpentylene (—CH$_2$—CH(CH$_3$)—CH$_2$—CH$_2$—CH$_2$—), 3-methylpentylene (—CH$_2$—CH$_2$—CH(CH$_3$)—CH$_2$—CH$_2$—), 4-methylpentylene (—CH$_2$—CH$_2$—CH$_2$—CH(CH$_3$)—CH$_2$—), 5-methylpentylene (—CH$_2$—CH$_2$—CH$_2$—CH$_2$—CH(CH$_3$)—), 1,2-dimethylbutylene (—CH(CH$_3$)—CH(CH$_3$)—CH$_2$—CH$_2$—), 1,3-dimethylbutylene (—CH(CH$_3$)—CH$_2$—CH(CH$_3$)—CH$_2$—), 1,4-dimethylbutylene (—CH(CH$_3$)—CH$_2$—CH$_2$—CH(CH$_3$)—), 2,3-dimethylbutylene (—CH$_2$—CH(CH$_3$)—CH(CH$_3$)—CH$_2$—), 2,4-dimethylbutylene (—CH$_2$—CH(CH$_3$)—CH$_2$—CH(CH$_3$)—), 3,4-dimethylbutylene (—CH$_2$—CH$_2$—CH(CH$_3$)—CH(CH$_3$)—).

When Y represents an unsaturated linear or branched alkylene group, it can be chosen from the group comprising: vinylene (—CH═CH—), ethynylene (—C≡C—), prop-1-enylene (—C═CH—CH$_2$—), prop-2-enylene (—CH$_2$—CH═CH—), propanedienylene (—CH═C═CH—), prop-1-ynylene (—C≡C—CH$_2$—), prop-2-ynylene (—CH$_2$—C≡C—), but-1-enylene (—CH═CH—CH$_2$—CH$_2$—), cis or trans but 2-enylene (—CH$_2$—CH═CH—CH$_2$—), but-3-enylene (—CH$_2$—CH$_2$—CH═CH—), but-1,2-dienylene (—CH═CH═CH—CH$_2$—), but-1,3 dienylene (—CH═CH$_2$—CH═CH—), but-1,2,3 trienylene (—CH═CH═CH═CH—), but-1-ynylene (—C≡C—CH$_2$—CH$_2$—), but-2-ynylene (—CH$_2$—C≡C—CH$_2$—), but-3-ynylene (—CH$_2$—CH$_2$—CC—), but-1,3 diynylene (—C≡C—C≡C—).

Within the context of the invention, an aryl group is a group derived from an aromatic ring. Preferentially, the aryl group corresponds to a phenyl or a naphthyl.

The $C_3$-$C_6$ cycloalkyls of the invention can be chosen from the following rings: cyclopropyl, cyclobutyl, cyclopentyl and cyclohexyl.

The halogen atoms defined in the invention are preferentially chosen from fluorine (F), chlorine (Cl) bromine (Br) and iodine (I).

In a preferred embodiment, the invention relates to the abovementioned compounds of general formula (Ia) below:

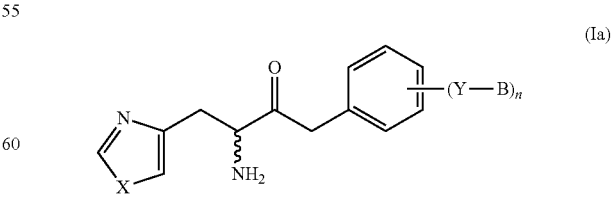

where X is a heteroatom chosen from the elements of the chalcogen or pnictogen family, and preferably where X is a heteroatom chosen from oxygen (O), sulphur (S) and nitrogen (N).

In a more preferred embodiment, a subject of the invention is compounds of general formula (Ia), where X represents nitrogen (N).

One of the preferred embodiments of the invention relates to the compounds mentioned previously, of general formula (Ib) below:

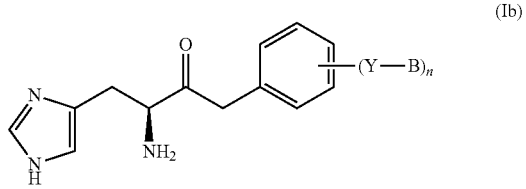

(Ib)

The compounds of general formula (Ib) correspond to a particular enantiomer of the compounds of general formula Ia, i.e. the compounds of configuration S.

These compounds are substituted derivatives of L-histidine phenyl.

Another preferred embodiment of the invention relates to compounds, defined by general formulae Ia or Ib, characterized in that said compounds are monosubstituted by a Y—B group, said Y—B group being such that:
  Y represents a single bond, a $C_1$-$C_3$ alkylene, a $C_2$-$C_3$ alkenylene or a $C_2$-$C_3$ alkynylene, and
  B represents an aryl or heteroaryl group, preferentially a phenyl group, optionally substituted by:
    a hydrogen atom,
    a halogen atom,
    an alkoxy group comprising from 1 to 4 carbon atoms,
    an aryloxy group, in particular a phenyloxy group
    a saturated or unsaturated, linear, branched or cyclic alkyl group, comprising from 1 to 6 carbon atoms, preferably from 2 to 4 carbon atoms, optionally substituted by one or more halogen atoms, and
    an aryl group, preferentially a phenyl group, optionally substituted by a $C_1$-$C_4$ alkyl,
    a hydroxyl group,
    a thiol group,
    a primary, secondary or ternary amine group
    an amide group,
    a carboxylic acid group, and
    a cyano group.
    an azide group
    a nitro group In said preferred embodiment of the invention, the Y group is either a single bond, or a $C_1$ (methylene; —$CH_2$—), $C_2$ (ethylene; —$CH_2$—$CH_2$—) or $C_3$ (propylene; —$CH_2$—$CH_2$—$CH_2$—) alkylene, or a C2 (vinylene; —CH═CH—) or C3 (prop-1-enylene; —CH═CH—$CH_2$—, or prop-2-enylene; —$CH_2$—CH═CH—) alkenylene, said alkenylenes being preferentially in trans (opposite) configuration, or a C2 (ethylylene; —C≡C—) or C3 (prop-1-ynylene; —C≡C—$CH_2$—, or prop-2-ynylene; —$CH_2$—C≡C—) alkynylene.

In a preferred embodiment, a subject of the invention is the compounds of formula (Ia) or (Ib) in which the Y—B group is in the para position of the phenyl group.

Another embodiment of the invention relates to the abovementioned compounds, where:
  Y represents a single bond, and
  B represents
    a naphthyl group or
    a phenyl group substituted, preferentially in the para position, by
      a saturated or unsaturated, linear, branched or cyclic alkyl group, comprising from 1 to 6 carbon atoms, preferably from 2 to 4 carbon atoms, said alkyl group being optionally substituted by one or more halogen atoms,
      an aryloxy group, in particular a phenoxy,
      a C1-C4 alkoxy group,
      a halogen, or
      a phenyl group, optionally substituted by a $C_1$-$C_4$ alkyl,
said compounds being in particular the compounds of formula Ib.2a, Ib.2b, Ib.2c, Ib.2d, Ib.2e, Ib.2f, Ib.2g, or Ib.2h.

Another embodiment of the invention relates to the abovementioned compounds, where:
  Y represents a $C_1$-$C_3$ alkylene, and
  B represents a phenyl group
said compounds being in particular the compound of formula Ib.2i.

Another embodiment of the invention relates to the abovementioned compounds, where:
  Y represents a $C_2$-$C_3$ alkenylene, and
  B represents a phenyl group, optionally substituted by
    a saturated or unsaturated, linear, branched or cyclic alkyl group, comprising from 1 to 6 carbon atoms, preferably from 2 to 4 carbon atoms, optionally substituted by one or more halogen atoms, or
    an aryl group, in particular a phenyl
said compounds being in particular the compound of formula Ib.2j, Ib.2k, Ib.2l or Ib.2m.

Another embodiment of the invention relates to the abovementioned compounds, where:
  Y represents a $C_2$-$C_3$ alkynylene, and
  B represents a phenyl group, optionally substituted by
    a saturated or unsaturated, linear, branched or cyclic alkyl group, comprising from 1 to 6 carbon atoms, preferably from 2 to 4 carbon atoms, or
    an aryl group, in particular a phenyl
said compounds being in particular the compound of formula Ib.3a, Ib.3b, Ib.3c or Ib.3e.

Another preferred embodiment of the invention relates to the above mentioned compounds, said compounds being chosen from the following compounds:

| Formula no. | Structure | name |
|---|---|---|
| (Ib.2a) | 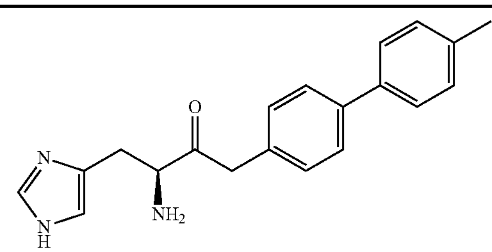 | (3S)-3-amino-4-(1H-imidazol-4-yl)-1-(4'-methylbiphenyl-4-yl)butan-2-one |

-continued
| Formula no. | Structure | name |
|---|---|---|
| (Ib.2b) | 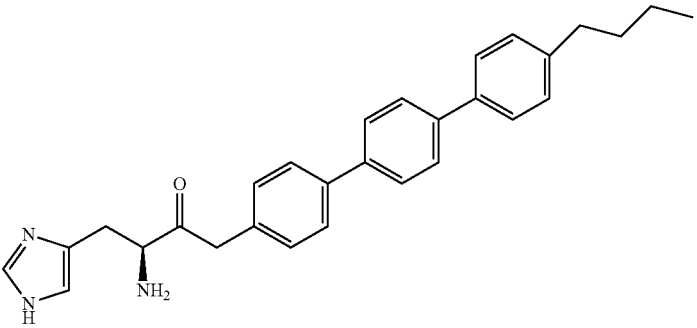 [SMILES: CCCCc1ccc(-c2ccc(-c3ccc(CC(=O)[C@@H](N)Cc4c[nH]cn4)cc3)cc2)cc1] | (3S)-3-amino-1-(4'-butylbiphenyl-4-yl)-4-(1H-imidazol-4-yl)butan-2-one |
| (Ib.2c) | 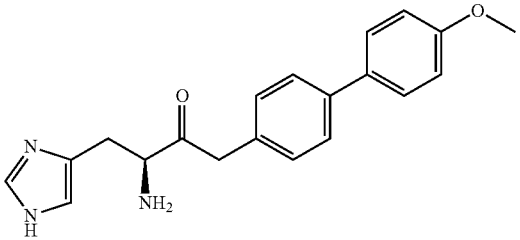 [SMILES: COc1ccc(-c2ccc(CC(=O)[C@@H](N)Cc3c[nH]cn3)cc2)cc1] | (3S)-3-amino-4-(1H-imidazol-4-yl)-1-(4'-methoxybiphenyl-4-yl)butan-2-one |
| (Ib.2d) | 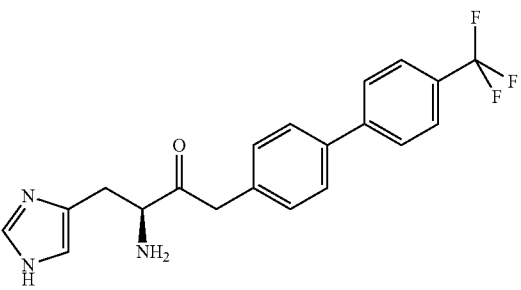 [SMILES: N[C@@H](Cc1c[nH]cn1)C(=O)Cc1ccc(-c2ccc(C(F)(F)F)cc2)cc1] | (3S)-3-amino-4-(1H-imidazol-4-yl)-1-[4'-(trifluoromethyl)biphenyl-4-yl]butan-2-one |
| (Ib.2e) | 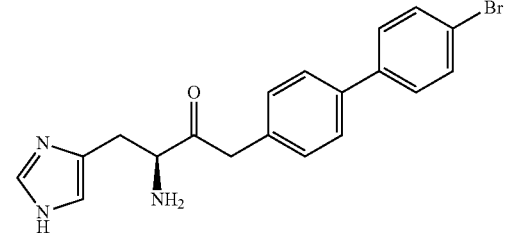 [SMILES: N[C@@H](Cc1c[nH]cn1)C(=O)Cc1ccc(-c2ccc(Br)cc2)cc1] | (3S)-3-amino-1-(4'-bromobiphenyl-4-yl)-4-(1H-imidazol-4-yl)butan-2-one |
| (Ib.2f) | 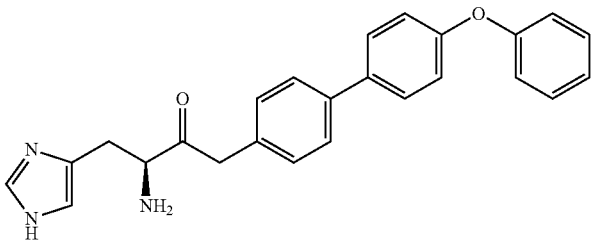 [SMILES: N[C@@H](Cc1c[nH]cn1)C(=O)Cc1ccc(-c2ccc(Oc3ccccc3)cc2)cc1] | (3S)-3-amino-4-(1H-imidazol-4-yl)-1-(4'-phenoxybiphenyl-4-yl)butan-2-one |

-continued

| Formula no. | Structure | name |
|---|---|---|
| (Ib.2g) | 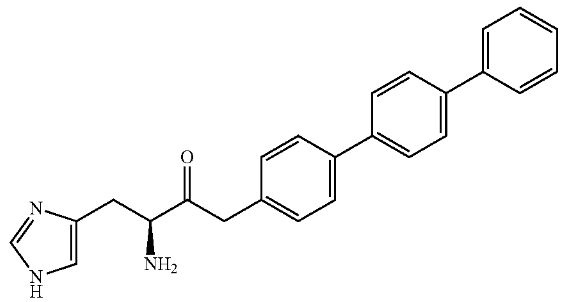 [SMILES: N[C@@H](Cc1c[nH]cn1)C(=O)Cc1ccc(-c2ccc(-c3ccccc3)cc2)cc1] | (3S)-3-amino-4-(1H-imidazol-4-yl)-1-(1,1':4',1''-terphenyl-4-yl)butan-2-one |
| (Ib.2h) | 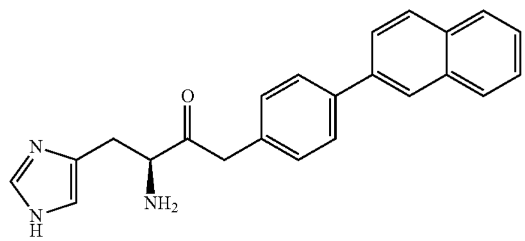 [SMILES: N[C@@H](Cc1c[nH]cn1)C(=O)Cc1ccc(-c2ccc3ccccc3c2)cc1] | (3S)-3-amino-4-(1H-imidazol-4-yl)-1-[4-(2-naphthhyl)phenyl]butan-2-one |
| (Ib.2i) | 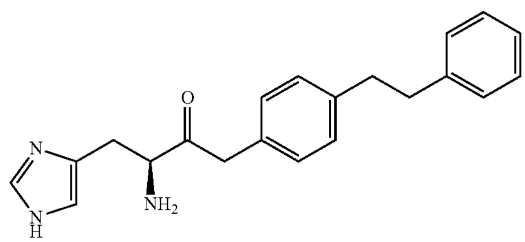 [SMILES: N[C@@H](Cc1c[nH]cn1)C(=O)Cc1ccc(CCc2ccccc2)cc1] | (3S)-3-amino-4-(1H-imidazol-4-yl)-1-[4-(2-phenylethyl)phenyl]butan-2-one |
| (Ib.2j) | 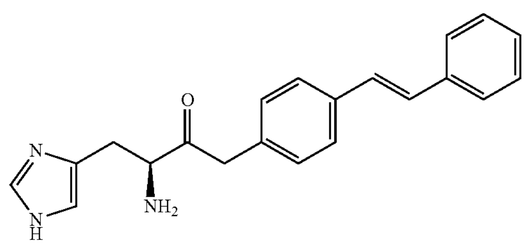 [SMILES: N[C@@H](Cc1c[nH]cn1)C(=O)Cc1ccc(/C=C/c2ccccc2)cc1] | (3S)-3-amino-4-(1H-imidazol-4-yl)-1-{4-[(E)-2-phenylvinyl]phenyl}butan-2-one |
| (Ib.2k) | 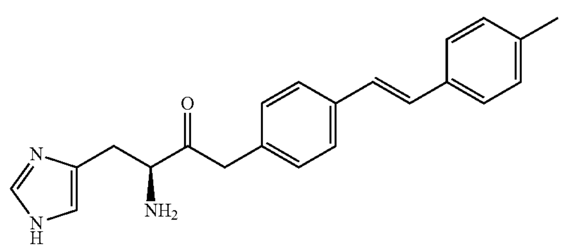 [SMILES: Cc1ccc(/C=C/c2ccc(CC(=O)[C@@H](N)Cc3c[nH]cn3)cc2)cc1] | (3S)-3-amino-4-(1H-imidazol-4-yl)-1-{4-[(E)-2-(4-methylphenyl)vinyl]phenyl}butan-2-one |
| (Ib.2l) | 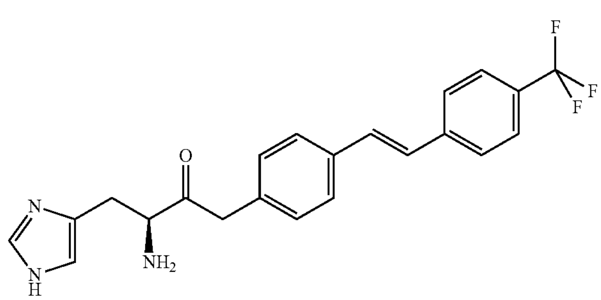 [SMILES: N[C@@H](Cc1c[nH]cn1)C(=O)Cc1ccc(/C=C/c2ccc(C(F)(F)F)cc2)cc1] | (3S)-3-amino-4-(1H-imidazol-4-yl)-1-(4-{(E)-2-[4-(trifluoromethyl)phenyl]vinyl}phenyl)butan-2-one |

| Formula no. | Structure | name |
|---|---|---|
| (Ib.2m) | 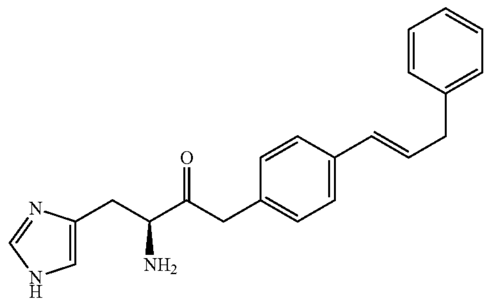 [SMILES: N[C@@H](Cc1c[nH]cn1)C(=O)Cc1ccc(/C=C/Cc2ccccc2)cc1] | (3S)-3-amino-4-(1H-imidazol-4-yl)-1-{4-[(1E)-3-phenylprop-1-en-1-yl]phenyl}butan-2-one |
| (Ib.2n) | 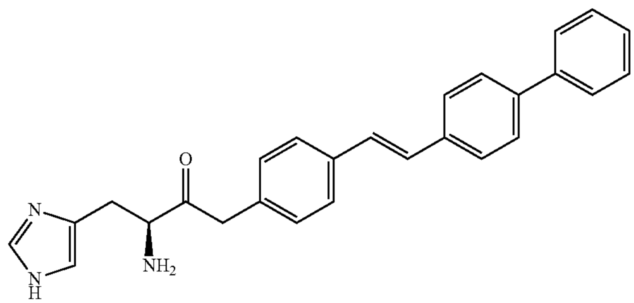 [SMILES: N[C@@H](Cc1c[nH]cn1)C(=O)Cc1ccc(/C=C/c2ccc(-c3ccccc3)cc2)cc1] | (3S)-3-amino-1-{4-[(E)-2-biphenyl-4-ylvinyl]phenyl}-4-(1H-imidazol-4-yl)butan-2-one |
| (Ib.3a) | 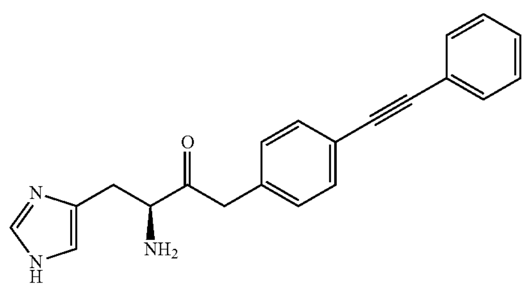 [SMILES: N[C@@H](Cc1c[nH]cn1)C(=O)Cc1ccc(C#Cc2ccccc2)cc1] | (3S)-3-amino-4-(1H-imidazol-4-yl)-1-[4-(phenylethynyl)phenyl]butan-2-one |
| (Ib.3b) | 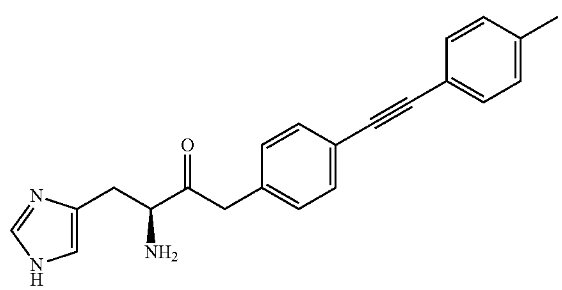 [SMILES: Cc1ccc(C#Cc2ccc(CC(=O)[C@@H](N)Cc3c[nH]cn3)cc2)cc1] | (3S)-3-amino-4-(1H-imidazol-4-yl)-1-{4-[(4-methylphenyl)ethynyl]phenyl}butan-2-one |
| (Ib.3c) | 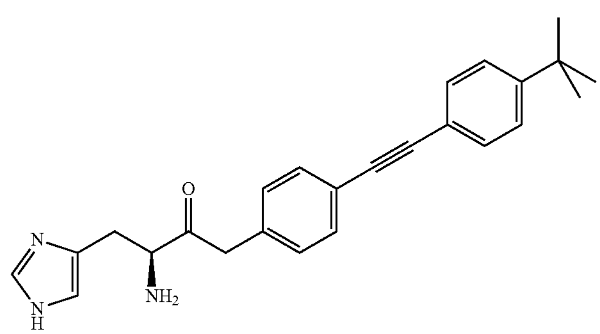 [SMILES: CC(C)(C)c1ccc(C#Cc2ccc(CC(=O)[C@@H](N)Cc3c[nH]cn3)cc2)cc1] | (3S)-3-amino-1-{4-[(4-tert-butylphenyl)ethynyl]phenyl}-4-(1H-imidazol-4-yl)butan-2-one |

| Formula no. | Structure | name |
|---|---|---|
| (Ib.3d) | 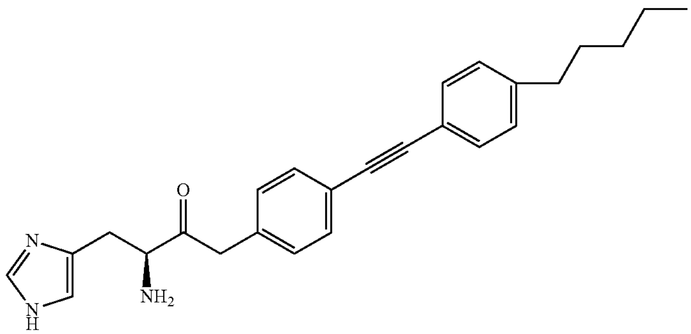 [SMILES: CCCCCc1ccc(C#Cc2ccc(CC(=O)[C@@H](N)Cc3c[nH]cn3)cc2)cc1] | (3S)-3-amino-4-(1H-imidazol-4-yl)-1-{4-[(4-pentylphenyl)ethynyl]phenyl}butan-2-one |
| (Ib.3e) | 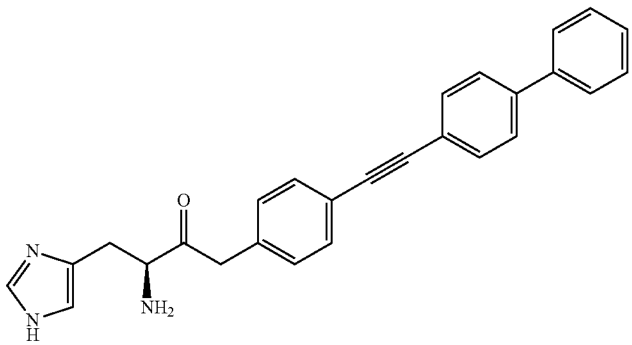 [SMILES: N[C@@H](Cc1c[nH]cn1)C(=O)Cc1ccc(C#Cc2ccc(-c3ccccc3)cc2)cc1] | (3S)-3-amino-1-[4-(biphenyl-4-ylethynyl)phenyl]-4-(1H-imidazol-4-yl)butan-2-one |

The compounds according to the invention can be synthesized by any process known to a person skilled in the art, starting from commercially available products. The synthesis of certain compounds of the invention is presented in the examples hereafter.

A subject of the invention is also the previous compounds, as medicaments.

Also, one of the advantageous embodiments of the invention relates to pharmaceutical compositions comprising as active ingredient at least one of the previous compounds, in combination with a pharmaceutically acceptable vehicle.

The advantageous compositions according to the invention are characterized in that they inhibit the activity of histidinol dehydrogenase and inhibit the intracellular proliferation of bacteria. The inhibition of the activity of the enzyme and of the proliferation is measured according to the tests described in the experimental part. The inhibition of histidinol dehydrogenase is evaluated by determining the inhibition of 50% of the enzyme conversion activity at a given concentration of the inhibitor, and the inhibition of the proliferation is evaluated by measuring the reduction (as a function of the inhibitor concentration) in proliferation compared to proliferation in the absence of inhibitor compounds.

The dosage of the active ingredient depends particularly on the method of administration, and is easily determined by a person skilled in the art.

For example, without however being limitative, the compositions as defined in the invention are characterized in that they are capable of being administered by intravenous route at a rate of 5 to 90 µg/kg/day in humans.

One of the preferred embodiments of the invention relates to above-mentioned compounds or pharmaceutical compositions, for the treatment or prevention of infections caused by microorganisms, in particular bacteria or fungi such as yeasts.

In an advantageous embodiment of the invention, said microorganisms are microorganisms expressing the enzyme histidinol dehydrogenase.

In a preferred embodiment of the invention, said microorganisms are bacteria, in particular bacteria of the genera *Brucella* or *Mycobacterium*.

Within the context of the invention, the bacteria of the genus *Brucella* are represented by: *Brucella abortus, Brucella canis, Brucella melitensis, Brucella neotomae, Brucella ovis, Brucella suis, Brucella pinnipediae, Brucella cetaceae* and *Brucella microti*.

Moreover, within the context of the invention, the bacteria of the genus *Mycobacterium* are represented by: *Mycobacterium abscessus, Mycobacterium africanum, Mycobacterium agri, Mycobacterium aichiense, Mycobacterium alvei, Mycobacterium arupense, Mycobacterium asiaticum, Mycobacterium aubagnense, Mycobacterium aurum, Mycobacterium austroafricanum, Mycobacterium avium* complex (MAC), comprising, *Mycobacterium avium, Mycobacterium avium paratuberculosis, Mycobacterium avium silvaticum, Mycobacterium avium "hominissuis", Mycobacterium colombiense, Mycobacterium boenickei, Mycobacterium bohemicum, Mycobacterium bolletii, Mycobacterium botniense, Mycobacterium bovis, Mycobacterium branderi, Mycobacterium brisbanense, Mycobacterium brumae, Mycobacterium canariasense, Mycobacterium caprae, Mycobacterium celatum, Mycobacterium chelonae, Mycobacterium chimaera, Mycobacterium chitae, Mycobacterium chlorophenolicum, Mycobacterium chubuense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogens, Mycobacterium flave-*

*scens, Mycobacterium florentinum, Mycobacterium fluoroanthenivorans, Mycobacterium fortuitum, Mycobacterium fortuitum* subsp. *acetamidolyticum, Mycobacterium frederiksbergense, Mycobacterium gadium, Mycobacterium gastri, Mycobacterium genavense, Mycobacterium gilvum, Mycobacterium goodii, Mycobacterium gordonae, Mycobacterium haemophilum, Mycobacterium hassiacum, Mycobacterium heckeshornense, Mycobacterium heidelbergense, Mycobacterium hiberniae, Mycobacterium hodleri, Mycobacterium holsaticum, Mycobacterium houstonense, Mycobacterium immunogenum, Mycobacterium interjectum, Mycobacterium intermedium, Mycointracellular bacteriume, Mycobacterium kansasii, Mycobacterium komossense, Mycobacterium kubicae, Mycobacterium kumamotonense, Mycobacterium lacus, Mycobacterium lentiflavum, Mycobacterium leprae, Mycobacterium lepraemurium, Mycobacterium madagascariense, Mycobacterium mageritense, Mycobacterium malmoense, Mycobacterium marinum, Mycobacterium massiliense, Mycobacterium microti, Mycobacterium monacense, Mycobacterium montefiorense, Mycobacterium moriokaense, Mycobacterium mucogenicum, Mycobacterium murale, Mycobacterium nebraskense, Mycobacterium neoaurum, Mycobacterium neworleansense, Mycobacterium nonchromogenicum, Mycobacterium novocastrense, Mycobacterium obuense, Mycobacterium palustre, Mycobacterium parafortuitum, Mycobacterium parascrofulaceum, Mycobacterium parmense, Mycobacterium peregrinum, Mycobacterium phlei, Mycobacterium phocaicum, Mycobacterium pinnipedii, Mycobacterium porcinum, Mycobacterium poriferae, Mycobacterium pseudoshottsii, Mycobacterium pulveris, Mycobacterium psychrotolerans, Mycobacterium pyrenivorans, Mycobacterium rhodesiae, Mycobacterium saskatchewanense, Mycobacterium scrofulaceum, Mycobacterium senegalense, Mycobacterium seoulense, Mycobacterium septicum, Mycobacterium shimoidei, Mycobacterium shottsii, Mycobacterium simiae, Mycobacterium smegmatis, Mycobacterium sphagni, Mycobacterium szulgai, Mycobacterium terrae, Mycobacterium thermoresistibile, Mycobacterium tokaiense, Mycobacterium triplex, Mycobacterium triviale, Mycobacterium tuberculosis* complex (MTBC), comprising *Mycobacterium tuberculosis, Mycobacterium bovis, Mycobacterium bovis* BCG, *Mycobacterium africanum, Mycobacterium canetti, Mycobacterium caprae, Mycobacterium pinnipedii', Mycobacterium tusciae, Mycobacterium ulcerans, Mycobacterium vaccae, Mycobacterium vanbaalenii, Mycobacterium wolinsky* and *Mycobacterium xenopi.*

Also, in a particular embodiment, a subject of the invention is the use of the previous compounds for producing a medicament intended for the treatment or prevention of bacterial infections.

Similarly, the invention relates to a method for treating bacterial infections comprising the administration to subjects, or patients, as needed, previously-described compounds or pharmaceutical compositions, in therapeutically effective doses.

The dosage of the active ingredient depends particularly on the method of administration, and is easily determined by a person skilled in the art.

The treatment of the invention, without however being limitative, can be administered by intravenous route at a rate of 5 to 90 μg/kg/day.

The compounds or the pharmaceutical compositions of the invention can be administered in particular by intravenous route, by sub-cutaneous route, by systemic route, or by local route by means of infiltrations or orally.

The treatment can be continuous or sequential, i.e. by means of a perfusion delivering said compounds or pharmaceutical compositions in a continuous and optionally constant manner, or discontinuously, by one or more daily administrations or injections, optionally repeated over several days, either consecutive, or with latency with no treatment between the administrations.

The present invention is illustrated by the following figures and examples. The examples illustrate, without however being limited to, the preferred embodiments of the invention described previously.

Examples 1 to 3 illustrate the methods of synthesis of the different compounds of the invention. Examples 4 to 6 illustrate the properties of the compounds of the invention on the strain *B. suis.*

FIG. 1 represents the curve of intracellular survival of *Brucella suis* in the macrophage in the absence and in the presence of inhibitor.

The axis of the abscissa (x) represents the time expressed in hours, the axis of the ordonate (y) represents the logarithm of the number of colonies of *Brucella* (CFU) per well of infected macrophages. The curve with the solid circles (•) represents the control, the curve with the open triangles (Δ) represents the cells treated with 5 μM of compound Ib 3a, and the curve with the black triangles (▲) represents the cells treated with 10 μM of compound Ib 3a.

EXAMPLES

In the series of reactions hereafter, all the solutions as well as the solvents were degassed by a flow of argon before being used. The reactions were carried out on the scale of 0.2 g of the starting precursor.

The different compounds originate from Aldrich, Fluka or Alfa-Aesar. They were used in the reactions without particular previous treatment.

Example 1

General Procedure for the Cross-coupling of Different Substituted Boronic Acids with the Parabrominated Precursor (1)

The parabrominated precursor of general formula (I) is prepared according to the process described in Abdo et al. *Bioorg. Med. Chem.* 15 (2007): 4427-4433.

The parabrominated precursor (1 eq.) as well as 5 ml of toluene are introduced into a 50 ml two-necked flask provided with a cooler and a magnetic stirring bar under an argon flow. In parallel, 3 eq of the corresponding boronic acid is dissolved in a minimum amount of ethanol in another 10 ml flask and under an inert atmosphere. This solution is then transferred into the two-necked flask via a cannula. The catalyst $Pd(PPh_3)_4$ (0.1 eq.) is added under an intense argon flow, followed by 10 eq of an aqueous solution of $Na_2CO_3$ (1 M). The medium is taken to reflux and left under vigorous stirring for 12 hours. The reaction is monitored by mass spectroscopy analysis as the two starting and finishing products have the same frontal reports. Once the reaction is completed, the reaction medium is taken up with 50 ml of ethyl acetate and the organic phase is washed with water (3 times, 15 ml) then dried over anhydrous sodium sulphate. After evaporation of the solvent under reduced pressure the residue obtained is purified on a silica gel column ($CH_2Cl_2$/Hexane/Acetone: 5/4/1) in order to produce the protected final product. The latter is deprotected under acid conditions with a solution of HCl (4 M) in 1,4-dioxane. The reaction being completed (monitored by TLC), the precipitate obtained is filtered then washed several times with ethyl ether.

The synthesis reaction is as follows:

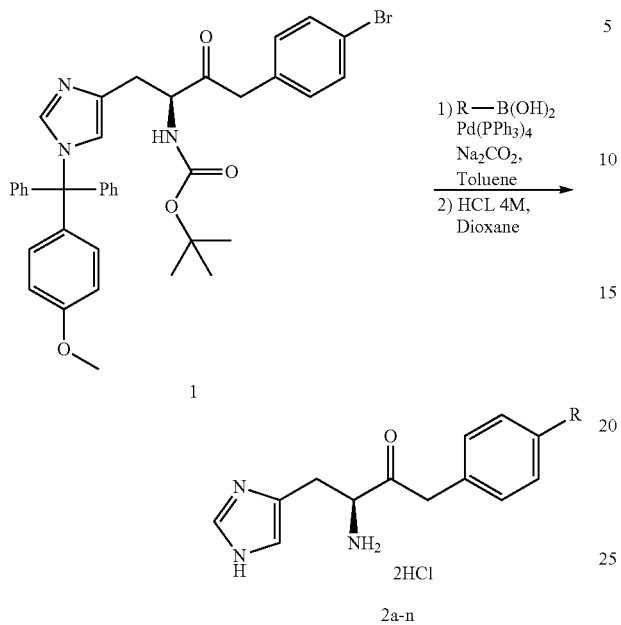

The different boronic acids used for the synthesis of the different compounds of the invention are as follows:

| Final product | Boronic acid used |
|---|---|
| Compound Ib 2a (2a) | 4-methylphenyl boronic acid |
| Compound Ib 2b (2b) | 4-butylphenyl boronic acid |
| Compound Ib 2c (2c) | 4-methoxyphenyl boronic acid |
| Compound Ib 2d (2d) | 4-trifluoromethylphenyl boronic acid |
| Compound Ib 2e (2e) | 4-bromophenyl boronic acid |
| Compound Ib 2f (2f) | 4-phenoxyphenyl boronic acid |
| Compound Ib 2g (2g) | 4-biphenyl boronic acid |
| Compound Ib 2h (2h) | 2-naphthyl boronic acid |
| Compound Ib 2i (2i) | 2-phenylethyl boronic acid |
| Compound Ib 2j (2j) | (E)-2-phenylvinyl boronic acid |
| Compound Ib 2k (2k) | (E)-2-(4-methylphenyl) vinyl boronic acid |
| Compound Ib 2l (2l) | (E)-2-(4-trifluoromethylphenyl) vinyl boronic acid |
| Compound Ib 2m (2m) | (1E)-3-phenyl 1-propene-1-yl boronic acid |
| Compound Ib 2n (2n) | (1E)-2-diphenylvinyl boronic acid |

Example 2

General Procedure for the Coupling of the Different Substituted Alkynes with the Parabrominated Precursor (1)

The parabrominated precursor of general formula (I) is prepared according to the process described in Abdo et al. *Bioorg. Med. Chem.* 15 (2007): 4427-4433 (1).

Parabrominated precursor (1 eq.) is dissolved in 10 ml of tetrahydrofuran (THF) in a 50 ml flask provided with a cooler and a magnetic stirring bar. The corresponding alkyne as well as $PPh_3$ (2 eq.) are added to this solution via a syringe. The medium being homogeneous, the base triethylamine (TEA) (3 eq.), cocatalyst CuI (0.2 eq.) as well as the catalyst $Pd(PPh_3)_4$ (0.1 eq.) are added. The mixture is then taken to reflux for 24 hours and monitored by mass spectroscopy analysis. The reaction medium is extracted with 50 ml of dichloromethane and washed with water (3 times, 15 ml). The organic phase is dried over anhydrous sodium sulphate and concentrated under reduced pressure. The residue obtained is directly chromatographed on silica gel ($PhCH_3/AcOEt$): (7/3) in order to produce the pure protected product. The latter is deprotected under acid conditions in a solution of HCl (4 M) in 1,4-dioxane. The reaction is monitored by TLC. At the end of the reaction, the precipitate obtained is filtered and washed several times with ethyl ether.

The synthesis reaction is as follows:

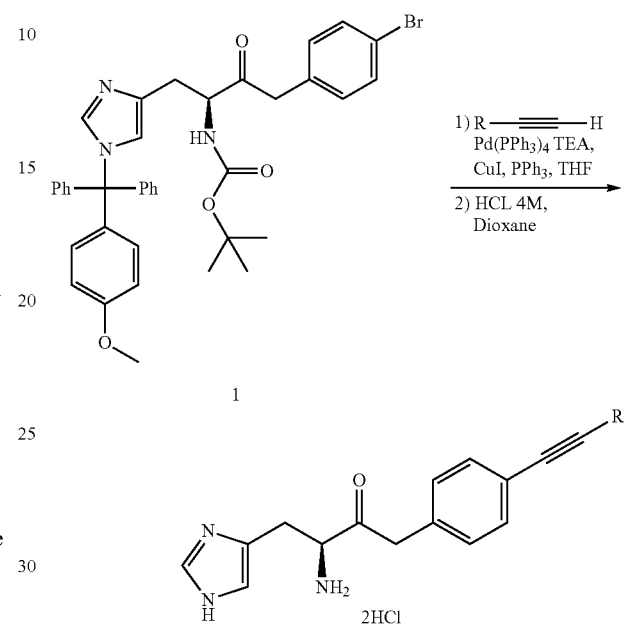

The different alkynes used for the synthesis of the different compounds of the invention are the following:

| Final product | Alkynes used |
|---|---|
| Compound Ib 3a (3a) | phenylethynyl |
| Compound Ib 3b (3b) | 4 methylphenylethynyl |
| Compound Ib 3c (3c) | 4 tertbutylphenylethynyl |
| Compound Ib 3d (3d) | 4 pentylphenylethynyl |
| Compound Ib 3e (3e) | biphenylethynyl |

Example 3

Spectroscopic and Spectrometric Analyses of the Different Compounds Obtained According to the Syntheses of Examples 1 and 2

General Conditions

Thin layer chromatographies (TLC) were carried out on Merck 60 F354 silica on aluminium plates. Depending on their nature, the products were developed in UV light (254 and 365 nm) in the case of the compounds possessing a chromophore group, or by spraying of a solution of ninhydrin in ethanol in the case of the amines. The purification of the compounds by column chromatography was carried out on a Carlo Erba silica gel (Silica Gel 60A, granulometry: 35-70 μm). The uncorrected melting points were determined in a capillary tube on a Büchi 530 device. The positive mode ($ESI^+$) or negative mode ($ESI^-$) Electro-Spray mass spectra were recorded on a Waters Micromass ZQ LCMS device. The proton and carbon 13 NMR spectra were recorded at ambient temperature on a Brüker DRX-400. The chemical shifts are expressed in ppm with respect to the DMSO signal fixed at 2.5 ppm. The multiplicity of the signals is indicated by one or more small letters: s (singlet), d (doublet), t (triplet), q (quadruplet), m (multiplet). The coupling constants J are expressed in Hertz (Hz). The solvents used were distilled according to the methods described by D. D Perrin and W. L. F. Amarego in Purification of Laboratory Chemicals, Permagon Press, London (1998).

The compounds obtained and their analyses are as follows:

(3S)-3-amino-4-(1H-imidazol-4-yl)-1-(4'-methylbiphenyl-4-yl)butan-2-one dihydrochlorhydrate (2a)

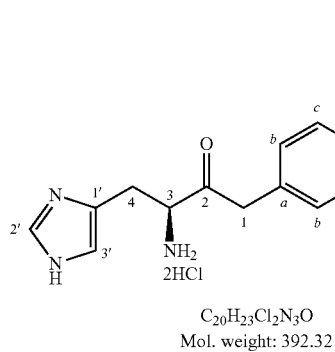

$C_{20}H_{23}Cl_2N_3O$
Mol. weight: 392.32

M.p. 203° C. (decomposition); MS (ESI$^+$/ESI$^-$): m/z 320 (M+H)$^+$, 639 (2M+H)$^+$; 318 (M–H)$^-$, 354 (M+Cl)$^-$, 673 (2M+Cl)$^-$; $^1$H NMR (400 MHz, DMSO-d$_6$) δ: 9.13 (d, J=1.1 Hz, 1H, $H_{2'}$), 8.65 (s, 3H, NH$_3^+$), 7.57 (dd, J=8.2 Hz, J=17.6 Hz, 4H, $H_{b,c,b',c'}$), 7.52 (s, 1H, $H_{3'}$), 7.29 (dd, J=8.1 Hz, J=21.8 Hz, 4H, $H_{b,c,b',c'}$), 4.73 (dd, J=4.1 Hz, J=7.9 Hz, 1H, $H_3$), 4.20 (s, 2H, $H_1$), 3.61 (dd, J=4.4 Hz, J=15.6 Hz, 1H, $H_4$), 3.24 (dd, J=8.9 Hz, J=15.5 Hz, 1H, $H_4$), 2.33 (s, 3H, $H_{e'}$); $^{13}$C NMR (101 MHz, DMSO-d$_6$) δ: 202.8 (1C, $C_2$), 138.6 (1C, $C_{d'}$), 136.9 (1C, $C_{d,a'}$), 136.6 (1C, $C_{d,a'}$), 134.1 (1C, $C_{2'}$), 132.2 (1C, $C_a$), 130.4 (2C, $C_{b,c,b',c'}$), 129.4 (2C, $C_{b,c,b',c'}$), 126.5 (1C, $C_{1'}$), 126.3 (2C, $C_{b,c,b',c'}$), 126.2 (2C, $C_{b,c,b',c'}$), 118.7 (1C, $C_{3'}$), 56.9 (1C, $C_3$), 44.9 (1C, $C_1$), 24.2 (1C, $C_4$), 20.6 (1C, $C_{e'}$).

(3S)-3-amino-1-(4'-butylbiphenyl-4-yl)-4-(1H-imidazol-4-yl) butan-2-one dihydrochlorhydrate (2b)

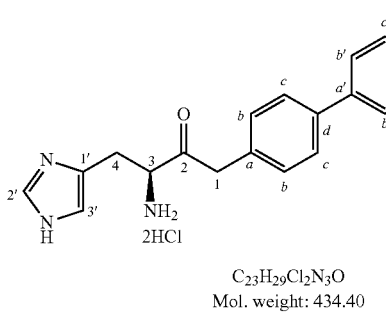

$C_{23}H_{29}Cl_2N_3O$
Mol. weight: 434.40

M.p. 155° C. (decomposition); MS (ESI$^+$/ESI$^-$): m/z 362 (M+H)$^+$, 723 (2M+H)$^+$; 360 (M–H)$^-$, 396 (M+Cl)$^-$, 757 (2M+Cl)$^-$; $^1$H NMR (400 MHz, DMSO-d$_6$) δ: 9.13 (d, J=1.3 Hz, 1H, $H_{2'}$), 8.62 (m, 3H, NH$_3^+$), 7.58 (dd, J=8.3 Hz, J=14.9 Hz, 4H, $H_{b,c,b',c'}$), 7.52 (d, J=0.9 Hz, 1H, $H_{3'}$), 7.30 (dd, J=8.3 Hz, J=18.1 Hz, 4H$_{b,c,b',c'}$), 4.73 (dd, J=4.3 Hz, J=9.0 Hz, 1H, $H_3$), 4.19 (s, 2H, $H_1$), 3.61 (dd, J=4.4 Hz, J=15.4 Hz, 1H, $H_4$), 3.23 (dd, J=8.9 Hz, J=15.5 Hz, 1H, $H_4$), 2.61 (t, J=7.74 Hz, 2H, $H_{e'}$), 1.57 (td, J=7.5 Hz, J=15.2 Hz, 2H, Hp), 1.32 (qd, J=7.3 Hz, J=14.5 Hz, 2H, $H_{g'}$), 0.90 (t, J=7.3 Hz, 3H, $H_{h'}$); $^{13}$C NMR (101 MHz, DMSO-d$_6$) δ: 202.8 (1C, $C_2$), 141.5 (1C, $C_{d'}$), 138.6 (1C, $C_{d,a'}$), 137.1 (1C, $C_{d,a'}$), 134.2 (1C, $C_a$), 132.2 (1C, $C_{1'}$), 130.4 (2C, $C_{b,c,b',c'}$), 128.8 (2C, $C_{b,c,b',c'}$), 126.5 (1C, $C_{1'}$), 126.3 (2C, $C_{b,c,b',c'}$), 126.3 (2C, $C_{b,c,b',c'}$), 118.3 (1C, $C_{3'}$), 56.9 (1C, $C_3$), 44.9 (1C, $C_1$), 34.3 (1C, $C_{e'}$), 33.0 (1C, $C_f$), 24.2 (1C, $C_4$), 21.7 (1C, $C_{g'}$), 13.7 (1C, $C_{h'}$)

(3S)-3-amino-4-(1H-imidazol-4-yl)-1-(4'-methoxybiphenyl-4-yl)butan-2-one dihydrochlorhydrate (2c)

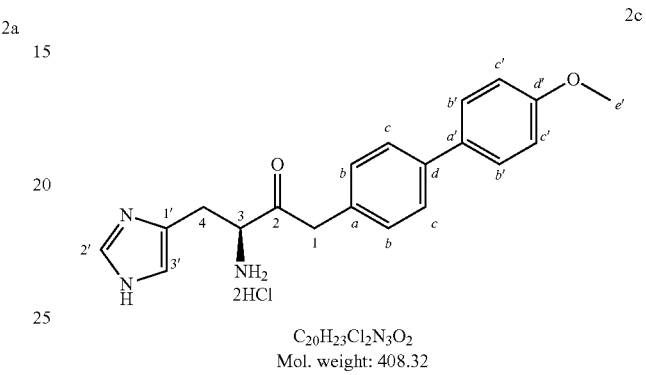

$C_{20}H_{23}Cl_2N_3O_2$
Mol. weight: 408.32

M.p. 210° C. (decomposition); MS (ESI$^+$/ESI$^-$): m/z 336 (M+H)$^+$, 671 (2M+H)$^+$; 334 (M–H)$^-$, 370 (M+Cl)$^-$, 705 (2M+Cl)$^-$; $^1$H NMR (400 MHz, DMSO-d$_6$) δ: 14.82 (s, 2H, NH$_2^+$), 9.13 (d, J=1.1 Hz, 1H, $H_{2'}$), 8.66 (s, 3H, NH$_3^+$), 7.58 (dd, J=8.6 Hz, J=11.4 Hz, 4H, $H_{b,c,b'}$), 7.52 (s, 1H, $H_{3'}$), 7.30 (d, J=8.3 Hz, 2H, $H_{b,c,b'}$), 7.01 (d, J=8.9 Hz, 2H, $H_{c'}$), 4.73 (dd, 1H, J=4.4 Hz, J=8.6 Hz, $H_3$), 4.19 (s, 2H, $H_1$), 3.79 (s, 3H, $H_{e'}$), 3.61 (dd, J=4.3 Hz, J=15.5 Hz, 1H, $H_4$), 3.25 (dd, J=8.9 Hz, J=15.4 Hz, 1H, $H_4$); $^{13}$C NMR (101 MHz, DMSO-d$_6$) δ: 202.9 (1C, $C_2$), 158.8 (1C, $C_{d'}$), 138.3 (1C, $C_d$), 134.1 (1C, $C_{2'}$), 132.1 (1C, $C_a$), 131.8 (1C, $C_{a'}$), 130.4 (2C, $C_{b,c,b'}$), 127.6 (2C, $C_{b,c,b'}$), 126.5 (1C, $C_{1'}$), 125.9 (2C, $C_{b,c,b'}$), 118.2 (1C, $C_{3'}$), 114.3 (2C, $C_{c'}$), 56.9 (1C, $C_3$), 55.1 (1C, $C_{e'}$), 44.9 (1C, $C_1$), 24.1 (1C, $C_4$)

(3S)-3-amino-4-(1H-imidazol-4-yl)-1-[4'-(trifluoromethyl) biphenyl-4-yl]butan-2-one dihydrochlorhydrate (2d)

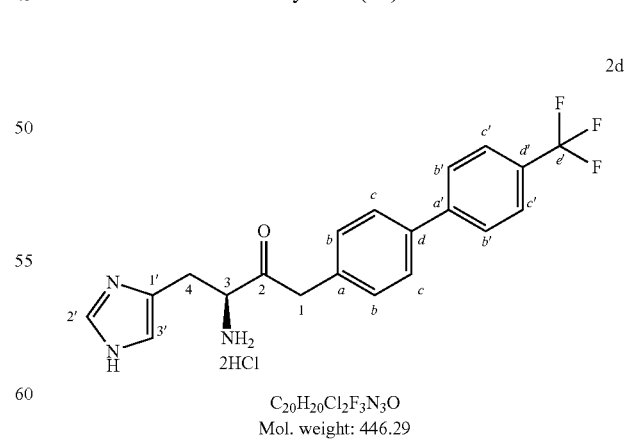

$C_{20}H_{20}Cl_2F_3N_3O$
Mol. weight: 446.29

M.p. 149° C. (decomposition); MS (ESI$^+$/ESI$^-$): m/z 374 (M+H)$^+$, 747 (2M+H)$^+$; 372 (M–H)$^-$, 408 (M+Cl)$^-$, 781 (2M+Cl)$^-$; $^1$H NMR (400 MHz, DMSO-d$_6$) δ: 14.78 (s, 2H, NH$_2^+$), 9.12 (d, J=1.3 Hz, 1H, $H_{2'}$), 8.64 (s, 3H, NH$_3^+$), 7.90 (d, J=8.2 Hz, 2H, $H_{b,c,b'}$), 7.81 (d, J=8.3 Hz, 2H, $H_{c'}$), 7.71 (d, J=8.4 Hz, 2H, $H_{b,c,b'}$), 7.52 (d, J=1.1 Hz, 1H, $H_{3'}$), 7.39 (d, J=8.4 Hz, 2H, $H_{b,c,b'}$), 4.75 (dd, J=4.6 Hz, J=8.9 Hz, 1H, $H_3$), 4.24 (s, 2H, $H_1$), 3.61 (dd, J=4.3 Hz, J=15.5 Hz, 1H, $H_4$), 3.24 (dd, J=8.9 Hz, J=15.5 Hz, 1H, $H_4$); $^{13}$C NMR (101 MHz, DMSO-$d_6$) δ: 202.7 (1C, $C_2$), 143.8 (1C, $C_a$), 137.0 (1C, $C_{a,d}$), 134.2 (1C, $C_{2'}$), 133.8 (1C, $C_{a,d}$), 130.6 (2C, $C_{b,c,b'}$), 127.8 (1C, $C_{d'}$), 127.3 (2C, $C_{b,c,b'}$), 126.8 (2C, $C_{b,c,b'}$), 126.6 (1C, $C_{1'}$), 125.7 (dd, J=3.6 Hz, J=7.3 Hz, 2C, $C_{e'}$), 122.9 (1C, $C_{e'}$), 118.2 (1C, $C_{3'}$), 56.9 (1C, $C_3$), 44.9 (1C, $C_1$), 24.2 (1C, $C_4$)

(3S)-3-amino-1-(4'-bromobiphenyl-4-yl)-4-(1H-imidazol-4-yl)butan-2-one dihydrochlorhydrate (2e)

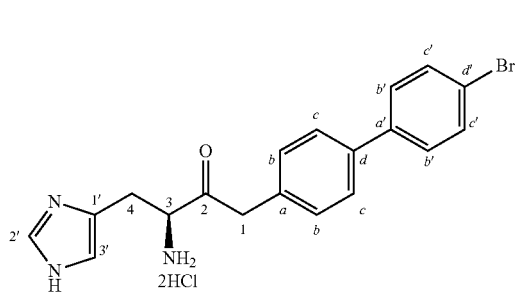

2e $C_{19}H_{20}BrCl_2N_3O$
Mol. weight: 457.19

M.p. 199° C. (decomposition); MS (ESI$^+$/ESI$^-$): m/z 383 (M+H)$^+$, 382 (M−H)$^-$, 416 (M+Cl)$^-$; $^1$H NMR (400 MHz, DMSO-$d_6$) δ: 14.51 (s, 2H, $NH_2^+$), 9.11 (d, J=1.0 Hz, 1H, $H_{2'}$), 8.59 (s, 3H, $NH_3^+$), 7.46 (m, 9H, $H_{b,c,b',c',3'}$), 4.70 (dd, J=4.2 Hz, J=9.1 Hz, 1H, $H_3$), 4.14 (s, 2H, $H_1$), 3.58 (dd, 1H, J=15.47, 4.33 Hz, $H_4$), 3.20 (dd, J=9.0 Hz, J=15.4 Hz, 1H, $H_4$); $^{13}$C NMR (101 MHz, DMSO-$d_6$) δ: 202.8 (1C, $C_2$), 134.2 (1C, $C_{2'}$), 133.3 (1C, $C_{a,d}$), 130.4 (1C, $C_{a,d}$), 129.8 (2C, $C_{b,c,b',c'}$), 128.9 (1C, $C_{a',d'}$), 128.9 (1C, $C_{a',d'}$), 128.2 (2C, $C_{b,c,b',c'}$), 127.1 (1C, $C_{1'}$), 126.8 (2C, $C_{b,c,b',c'}$), 126.5 (2C, $C_{b,c,b',c'}$), 118.2 (1C, $C_{3'}$), 56.9 (1C, $C_3$), 45.2 (1C, $C_1$), 24.2 (1C, $C_4$).

(3S)-3-amino-4-(1H-imidazol-4-yl)-1-(4'-phenoxybiphenyl-4-yl)butan-2-one dihydrochlorhydrate (2f)

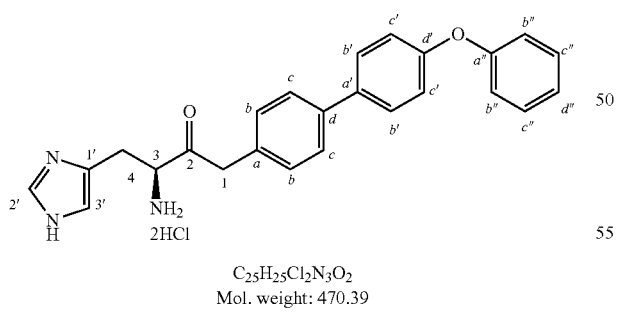

2f $C_{25}H_{25}Cl_2N_3O_2$
Mol. weight: 470.39

M.p. 198-200° C.; MS (ESI$^+$/ESI$^-$): m/z 398 (M+H)$^+$, 795 (2M+H)$^+$; 396 (M−H)$^-$, 432 (M+Cl)$^-$, 829 (2M+Cl)$^-$; $^1$H NMR (400 MHz, DMSO-$d_6$) δ: 14.81 (s, 2H, $NH_2^+$), 9.12 (d, J=1.08 Hz, 1H, $H_{2'}$), 8.66 (s, 3H, $NH_3^+$), 7.68 (d, J=8.76 Hz, 2H, $H_{b,c,b',c',b'',c''}$), 7.61 (d, J=8.26 Hz, 2H, $H_{b,c,b',c',b'',c''}$), 7.52 (s, 1H, $H_{3'}$), 7.42 (dd, J=8.53, 7.47 Hz, 2H, $H_{b,c,b',c',b'',c''}$), 7.33 (d, J=8.26 Hz, 2H, $H_{b,c,b',c',b'',c''}$), 7.17 (t, J=7.39, 7.39 Hz, 1H, $H_{d''}$), 7.11-7.04 (m, 4H, $H_{b,c,b',c',b'',c''}$), 4.74 (dd, J=8.70, 4.53 Hz, 1H, $H_3$), 4.20 (s, 2H, $H_1$), 3.61 (dd, J=15.46, 4.36 Hz, 1H, $H_4$), 3.24 (dd, J=15.48, 8.86 Hz, 1H, $H_4$); $^{13}$C NMR (101 MHz, DMSO-$d_6$) δ: 202.8 (1C, $C_2$), 156.4 (1C, $C_{d',a''}$), 156.3 (1C, $C_{d',a''}$), 137.9 (1C, $C_d$), 134.9 (1C, $C_a$), 134.1 (1C, $C_{2'}$), 132.3 (1C, $C_{a'}$), 130.4-128.1 (6C, $C_{b,c,b',c',b'',c''}$), 126.6 (1C, $C_{1'}$), 126.2 (2C, $C_{b,c,b',c',b'',c''}$), 123.6 (1C, $C_{d''}$), 118.8 (4C, $C_{b,c,b',c',b'',c''}$), 118.2 (1C, $C_{3'}$), 56.9 (1C, $C_3$), 44.9 (1C, $C_1$), 24.2 (1C, $C_4$).

(3S)-3-amino-4-(1H-imidazol-4-yl)-1-(1.1':4',1''-terphenyl-4-yl)butan-2-one dihydrochlorhydrate (2g)

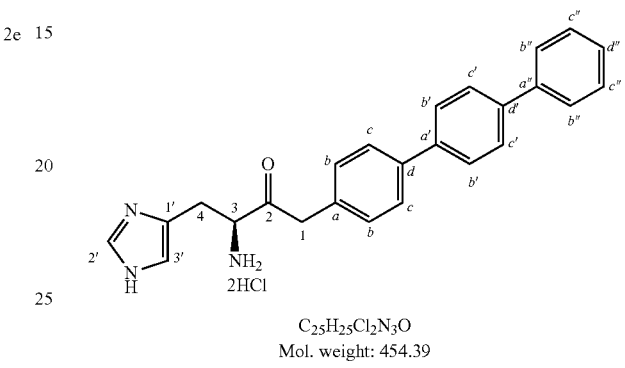

2g $C_{25}H_{25}Cl_2N_3O$
Mol. weight: 454.39

M.p. 200° C. (decomposition); MS (ESI$^+$/ESI$^-$): m/z 382 (M+H)$^+$, 763 (2M+H)$^+$; 380 (M−H)$^-$, 416 (M+Cl)$^-$, 797 (2M+Cl)$^-$; $^1$H NMR (400 MHz, DMSO-$d_6$) δ: 14.71 (s, 2H, $NH_2^+$), 9.12 (d, J=1.18 Hz, 1H, $H_{2'}$), 8.64 (s, 3H, $NH_3^+$), 7.77 (m, 4H, $H_{b,c,b',c',b'',c''}$), 7.75-7.65 (m, 4H, $H_{b,c,b',c',b'',c''}$), 7.52 (s, 1H, $H_{3'}$), 7.51-7.45 (m, 2H, $H_{b,c,b',c',b'',c''}$), 7.43-7.32 (m, 3H, $H_{b,c,b',c',b'',c'',d''}$), 4.75 (dd, J=8.70, 4.48 Hz, 1H, $H_3$), 4.22 (s, 2H, $H_1$), 3.62 (dd, J=15.47, 4.33 Hz, 1H, $H_4$), 3.24 (dd, J=15.52, 8.89 Hz, 1H, $H_4$); $^{13}$C NMR (101 MHz, DMSO-$d_6$) δ: 202.8 (1C, $C_2$), 139.5 (1C, $C_{d',a''}$), 139.0 (1C, $C_{d',a''}$), 138.7 (1C, $C_{d,a'}$), 138.1 (1C, $C_{d,a'}$), 134.2 (1C, $C_{2'}$), 132.7 (1C, $C_a$), 130.5 (2C, $C_{b,c,b',c',b'',c''}$), 128.9 (2C, $C_{b,c,b',c',b'',c''}$), 127.5 (1C, $C_{d''}$), 127.1 (2C, $C_{b,c,b',c',b'',c''}$), 127.0 (2C, $C_{b,c,b',c',b'',c''}$), 126.6 (1C, $C_{1'}$), 126.5 (2C, $C_{b,c,b',c',b'',c''}$), 126.4 (2C, $C_{b,c,b',c',b'',c''}$), 118.3 (1C, $C_{3'}$), 56.9 (1C, $C_3$), 44.9 (1C, $C_1$), 24.2 (1C, $C_4$).

(3S)-3-amino-4-(1H-imidazol-4-yl)-1-[4-(2-naphthyl)phenyl]butan-2-one dihydrochlorhydrate (2h)

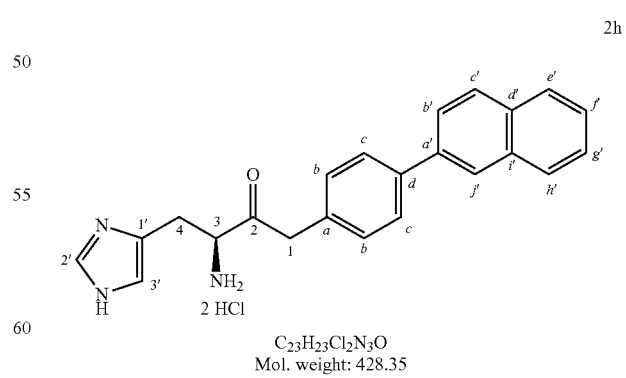

2h $C_{23}H_{23}Cl_2N_3O$
Mol. weight: 428.35

M.p. 205° C. (decomposition); MS (ESI$^+$/ESI$^-$): m/z 356 (M+H)$^+$, 713 (2M+H)$^+$; 354 (M−H)$^-$, 390 (M+Cl)$^-$, 745 (2M+Cl)$^-$; $^1$H NMR (400 MHz, DMSO-$d_6$) δ: 14.86 (s, 2H, $NH_2^+$), 9.14 (s, 1H, $H_{2'}$), 8.69 (s, 3H, $NH_3^+$), 8.22 (s, 1H, $H_{b',c',e',f,g',h',j'}$), 8.00 (m, 2H, $H_{b',c',e',f,g',h',j'}$), 7.94 (m, 1H, H$_{b',c',e',f,g',h',j'}$),7.85 (dd, J=1.6 Hz, J=8.6 Hz, 1H, H$_{b',c',e',f,g',h',j'}$), 7.79 (d, J=8.2 Hz, 2H, H$_c$),7.53 (m, 3H, H$_{b',c',e',f,g',h',j',3'}$), 7.40 (d, J=8.2 Hz, 2H, H$_b$), 4.76 (dd, J=4.7 Hz, J=8.7 Hz, 1H, H$_3$), 4.25 (s, 2H, H$_1$), 3.63 (dd, J=4.2 Hz, J=15.4 Hz, 1H, H$_4$), 3.27 (dd, J=9.1 Hz, J=15.6 Hz, 1H, H$_4$); $^{13}$C NMR (101 MHz, DMSO-d$_6$) δ: 202.8 (1C, C$_2$), 138.4 (1C, C$_{d,a'}$), 137.1 (1C, C$_{d,a'}$), 134.1 (1C, C$_{2'}$), 133.3 (1C, C$_a$), 132.8 (1C, C$_{d',i'}$), 132.1 (1C, C$_{d',i'}$), 130.5 (2C, C$_b$), 128.4-127.4 (3C, C$_{b',c',e',f,g',h',j'}$), 126.8 (2C, C$_c$), 126.6-126.0 (3C$_{b',c',e',f,g',h',j',1'}$), 125.0-124.9 (2C, C$_{b',c',e',f,g',h',j'}$), 118.3 (1C, C$_{3'}$), 56.9 (1C, C$_3$), 44.9 (1C, C$_1$), 24.2 (1C, C$_4$).

(3S)-3-amino-4-(1H-imidazol-4-yl)-1-[4-(2-phenyl-ethyl)phenyl] butan-2-one dihydrochlorhydrate (2i)

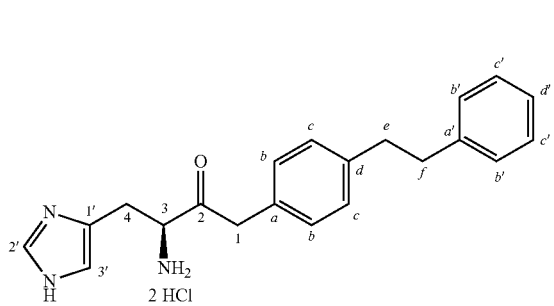

2i

C$_{21}$H$_{25}$Cl$_2$N$_3$O
Mol. weight: 406.35

M.p. 168-170° C.; MS (ESI$^+$/ESI$^-$): m/z 334 (M+H)$^+$, 667 (2M+H)$^+$; 332 (M−H)$^-$, 368 (M+Cl)$^-$, 701 (2M+Cl)$^-$; $^1$H NMR (400 MHz, DMSO-d$_6$) δ: 9.11 (s, 1H, H$_{2'}$), 8.63 (s, 3H, NH$_3^+$), 7.50 (s, 1H, H$_{3'}$), 7.31-7.20 (m, 4H, H$_{b,c,b',c'}$), 7.21-7.08 (m, 5H, H$_{b,c,e,f,b',c',d'}$), 4.69 (dd, J=8.03, 4.09 Hz, 1H, H$_3$), 4.10 (s, 2H, H$_1$), 3.57 (dd, J=15.41, 4.14 Hz, 1H, H$_4$), 3.21 (dd, J=15.39, 8.89 Hz, 1H, H$_4$), 2.86 (s, 4H, H$_{e,f}$); $^{13}$C NMR (101 MHz, DMSO-d$_6$) δ: 202.9 (1C, C$_2$), 141.4 (1C, C$_{a',d}$), 140.0 (1C, C$_{a',d}$), 134.1 (1C, C$_{2'}$), 130.7 (1C, C$_a$), 129.7-128.1 (8C, C$_{b,c,b',c'}$), 126.5 (1C, C$_1$), 125.7 (1C, C$_{d'}$), 118.2 (1C, C$_{3'}$), 56.9 (1C, C$_3$), 44.9 (1C, C$_1$), 36.9 (1C, C$_{e,f}$), 36.6 (1C, C$_{e,f}$), 24.1 (1C, C$_4$).

(3S)-3-amino-4-(1H-imidazol-4-yl)-1-{4-[(E)-2-phenylvinyl]phenyl}butan-2-one dihydrochlorhydrate (2j)

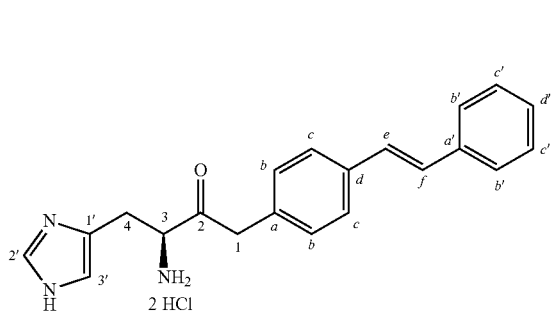

2j

C$_{21}$H$_{23}$Cl$_2$N$_3$O
Mol. weight: 404.33

M.p. 195° C. (decomposition); MS (ESI$^+$/ESI$^-$): m/z 332 (M+H)$^+$, 663(2M+H)$^+$;330 (M−H)$^-$, 366 (M+Cl)$^-$, 697 (2M+Cl)$^-$; $^1$H NMR (400 MHz, DMSO-d$_6$) δ: 14.58 (s, 2H, NH$_2^+$), 9.12 (d, J=1.4 Hz, 1H, H$_{2'}$), 8.61 (s, 3H, NH$_3^+$), 7.59 (m, 3H, H$_{b,c,b',c',d'}$), 7.51 (d, J=1.2 Hz, 1H, H$_{3'}$), 7.27 (m, 8H, H$_{b,c,b',c',d'}$), 4.72 (dd, J=4.5 Hz, J=8.6 Hz, 1H, H$_3$), 4.16 (s, 2H, H$_1$), 3.59 (dd, J=4.1 Hz, J=15.3 Hz, 1H, H$_4$), 3.22 (dd, J=8.9 Hz, J=15.5 Hz, 1H, H$_4$); $^{13}$C NMR (101 MHz, DMSO-d$_6$) δ: 202.8 (1C, C$_2$), 136.9 (1C, C$_{d,a'}$), 135.6 (1C, C$_{d,a'}$), 134.2 (1C, C$_{2'}$), 132.7 (1C, C$_a$), 130.2 (2C, C$_{b,c,b',c'}$), 128.6 (2C, C$_{b,c,b',c'}$), 128.2 (1C, C$_{e,f,d'}$), 127.9 (1C, C$_{e,f,d'}$), 127.6 (1C, C$_{e,f,d'}$), 126.5 (1C, C$_1$), 126.4 (2C, C$_{b,c,b',c'}$), 126.3 (2C, C$_{b,c,b',c'}$), 118.2 (1C, C$_{3'}$), 56.9 (1C, C$_3$), 45.0 (1C, C$_1$), 24.2 (1C, C$_4$).

(3S)-3-amino-4-(1H-imidazol-4-yl)-1-{4-[(E)-2-(4-methylphenyl) vinyl]phenyl}butan-2-one dihydrochlorhydrate (2k)

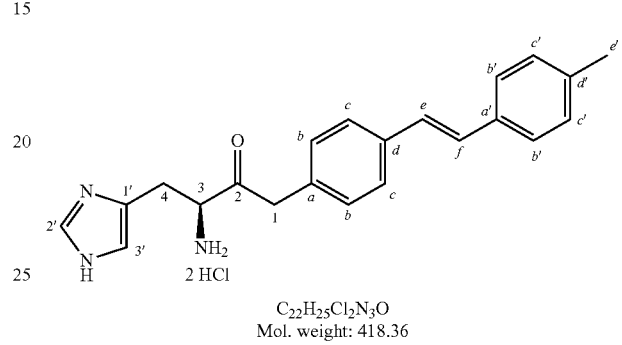

2k

C$_{22}$H$_{25}$Cl$_2$N$_3$O
Mol. weight: 418.36

M.p. 200° C. (decomposition); MS (ESI$^+$/ESI$^-$): m/z 346 (M+H)$^+$, 691 (2M+H)$^+$; 344 (M−H)$^-$, 380 (M+Cl)$^-$, 725 (2M+Cl)$^-$; $^1$H NMR (400 MHz, DMSO-d$_6$) δ: 14.56 (s, 2H, NH$_2^+$), 9.12 (d, J=1.3 Hz, 1H, H$_{2'}$), 8.61 (s, 3H, NH$_3^+$), 7.54 (d, J=8.3 Hz, 2H, H$_{b,c,b',c'}$), 7.51 (d, J=0.8 Hz, 1H, H$_{3'}$), 7.49 (d, J=8.2 Hz, 2H, H$_{b,c,b',c'}$), 7.24 (d, J=8.3 Hz, 2H, H$_{b,c,b',c'}$), 7.18 (m, 4H, H$_{b,c,e,f,b',c'}$), 4.71 (dd, J=4.5 Hz, J=8.0 Hz, 1H, H$_3$), 4.15 (s, 2H, H$_1$), 3.59 (dd, J=4.5 Hz, J=15.5 Hz, 1H, H$_4$), 3.22 (dd, J=9.0 Hz, J=15.5 Hz, 1H, H$_4$), 2.30 (s, 3H, H$_e$); $^{13}$C NMR (101 MHz, DMSO-d$_6$) δ: 202.8 (1C, C$_2$), 136.9 (2C, C$_{d,a'}$), 135.8 (1C, C$_{a,d}$), 134.2 (1C, C$_{2'}$), 132.5 (1C, C$_{a,d'}$), 130.2 (2C, C$_{b,c,b',c'}$), 129.2 (2C, C$_{b,c,b',c'}$), 128.1 (1C, C$_{e,f}$), 126.9 (1C, C$_{e,f}$), 126.5 (1C, C$_1$), 126.3 (2C, C$_{b,c,b',c'}$), 126.2 (2C, C$_{b,c,b',c'}$), 118.2 (1C, C$_{3'}$), 56.9 (1C, C$_3$), 45.0 (1C, C$_1$), 24.2 (1C, C$_4$), 20.8 (1C, C$_e$).

(3S)-3-amino-4-(1H-imidazol-4-yl)-1-(4-{(E)-2-[4-(trifluoro methyl)phenyl]vinyl}phenyl) butan-2-one dihydrochlorhydrate (2l)

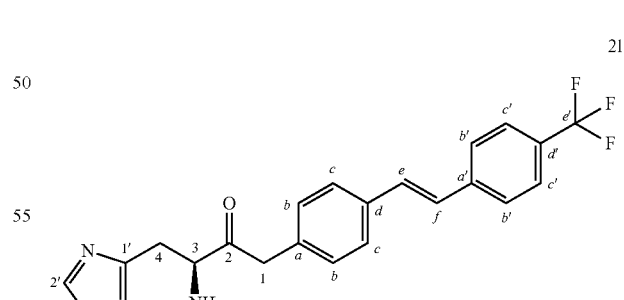

21

C$_{22}$H$_{22}$Cl$_2$F$_3$N$_3$O
Mol. weight: 472.33

M.p. 186° C. (decomposition); MS (ESI$^+$/ESI$^-$): m/z 399 (M+H)$^+$, 799 (2M+H)$^+$; 398 (M−H)$^-$, 434 (M+Cl)$^-$, 833 (2M+Cl)$^-$; $^1$H NMR (400 MHz, DMSO-d$_6$) δ: 14.56 (s, 2H, NH$_2^+$), 9.13 (s, 1H, H$_{2'}$), 8.62 (s, 3H, NH$_3^+$), 7.82 (d, J=8.1 Hz, 2H, H$_{b,c,b'}$), 7.72 (d, J=8.6 Hz, 2H, H$_{b,c,b'}$), 7.62 (d, J=8.2

Hz, 2H, H$_{b,c,b'}$), 7.52 (d, J=0.6 Hz, 1H, H$_{3'}$), 7.43 (d, J=16.6 Hz, 1H, H$_{e,f}$), 7.35 (d, J=16.4 Hz, 1H, H$_{e,f}$), 7.28 (d, J=8.1 Hz, 2H, H$_{c'}$), 4.72 (s 1H, H$_3$), 4.18 (s, 2H, H$_1$), 3.60 (dd, J=4.6 Hz, J=15.8 Hz, 1H, H$_4$), 3.22 (dd, J=9.2 Hz, J=15.5 Hz, 1H, H$_4$); $^{13}$C NMR (101 MHz, DMSO-d$_6$) δ: 202.7 (1C, C$_2$), 141.1 (1C, C$_{d,a'}$), 135.1 (1C, C$_{d,a'}$), 134.1 (1C, C$_{2'}$), 133.4 (1C, C$_a$), 130.9 (1C, C$_o$), 130.2 (2C, C$_{b,c,b'}$), 127.2 (1C, C$_{d'}$), 126.9 (2C, C$_{b,c,b'}$), 126.7 (2C, C$_{b,c,b'}$), 126.6 (1C, C$_{1'}$), 126.5 (1C, C$_{e,f}$), 125.5 (m, 2C, C$_{c'}$), 122.9 (1C, C$_e$), 118.2 (1C, C$_{3'}$), 56.9 (1C, C$_3$), 45.0 (1C, C$_1$), 24.1 (1C, C$_4$).

(3S)-3-amino-4-(1H-imidazol-4-yl)-1-{4-[(1E)-3-phenylprop-1-en-1-yl]phenyl}butan-2-one dihydrochlorhydrate (2m)

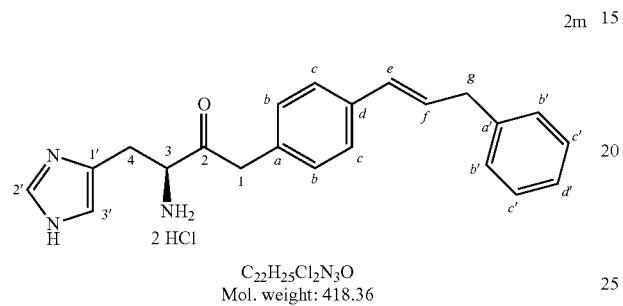

2m

C$_{22}$H$_{25}$Cl$_2$N$_3$O
Mol. weight: 418.36

M.p. 178-180° C.; MS (ESI$^+$/ESI$^-$): m/z 346 (M+H)$^+$, 691 (2M+H)$^+$; 344 (M−H)$^-$, 380 (M+Cl)$^-$, 725 (2M+Cl)$^-$; $^1$H NMR (400 MHz, DMSO-d$_6$) δ: 14.71 (s, 2H, NH$_2^+$), 9.11 (d, J=1.2 Hz, 1H, H$_{2'}$), 8.61 (s, 3H, NH$_3^+$), 7.50 (s, 1H, H$_{3'}$), 7.27 (m, 9H, H$_{b,c,b',c',d'}$), 6.47 (d, 1H, J=15.8 Hz, H$_e$), 6.41 (dd, 1H, J=16.5 Hz, J=6.1 Hz, H$_f$), 4.69 (dd, J=4.8 Hz, J=8.7 Hz, 1H, H$_3$), 4.12 (s, 2H, H$_1$), 3.57 (dd, J=4.3 Hz, J=15.6 Hz, 1H, H$_4$), 3.52 (d, J=5.6 Hz, 2H, H$_g$), 3.21 (dd, J=8.9 Hz, J=15.4 Hz, 1H, H$_4$); $^{13}$C NMR (101 MHz, DMSO-d$_6$) δ: 202.8 (1C, C$_2$), 139.9 (1C, C$_{d,a'}$), 135.6 (1C, C$_{d,a'}$), 134.1 (1C, C$_{2'}$), 132.1 (1C, C$_a$), 130.1 (1C, C$_e$), 130.0 (2C, C$_{b,c,b',c'}$), 129.2 (1C, C$_f$), 128.4 (2C, C$_{b,c,b',c'}$), 128.4 (2C, C$_{b,c,b',c'}$), 126.5 (1C, C$_{1'}$), 125.9 (1C, C$_{d'}$), 125.8 (2C, C$_{b,c,b',c'}$), 118.2 (1C, C$_{3'}$), 56.9 (1C, C$_3$), 44.9 (1C, C$_1$), 38.5 (1C, C$_g$), 24.1 (1C, C$_4$).

(3S)-3-amino-1-{4-[(E)-2-biphenyl-4-ylvinyl]phenyl}-4-(1H-imidazol-4-yl)butan-2-one dihydrochlorhydrate (2n)

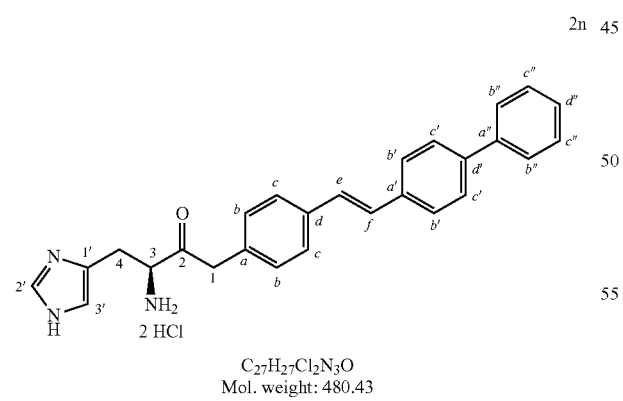

2n

C$_{27}$H$_{27}$Cl$_2$N$_3$O
Mol. weight: 480.43

M.p. 200° C. (decomposition); MS (ESI$^+$/ESI$^-$): m/z 408 (M+H)$^+$, 815 (2M+H)$^+$; 406 (M−H)$^-$, 442 (M+Cl)$^-$, 849 (2M+Cl)$^-$; $^1$H NMR (400 MHz, DMSO-d$_6$) δ: 14.54 (s, 2H, NH$_2^+$), 9.12 (d, J=1.3 Hz, 1H, H$_{2'}$), 8.59 (s, 3H, NH$_3^+$), 7.70 (m, 6H, H$_{b,c,b',c',b'',c''}$), 7.60 (d, J=8.4 Hz, 2H, H$_{b,c,b',c',b'',c''}$), 7.51 (d, J=1.0 Hz, 1H, H$_{3'}$), 7.47 (t, J=7.6 Hz, 2H, H$_{b,c,b',c',b'',c''}$), 7.37 (t, J=1.2 Hz, 1H, H$_{d''}$), 7.31 (m, 2H, H$_{b,c,b',c',b'',c''}$), 7.27 (d, J=8.3 Hz, 2H, H$_{b,c,b',c',b'',c'',d''}$), 4.72 (dd, J=4.3 Hz, J=8.3 Hz, 1H, H$_3$), 4.17 (s, 2H, H$_1$), 3.59 (dd, J=4.3 Hz, J=15.3 Hz, 1H, H$_4$), 3.22 (dd, J=8.9 Hz, J=15.5 Hz, 1H, H$_4$); $^{13}$C NMR (101 MHz, DMSO-d$_6$) δ: 202.8 (1C, C$_2$), 139.6 (1C, C$_{d,a',d',a''}$), 139.1 (1C$_{d,a',d',a''}$), 136.2 (1C, C$_{d,a',d',a''}$), 135.7 (1C, C$_{d,a',d',a''}$), 134.3 (1C, C$_{2'}$), 132.8 (1C, C$_a$), 130.3-126.4 (16C$_{b,c,b',c',b'',c''d'',e,f,1'}$), 118.3 (1C, C$_{3'}$), 56.9 (1C, C$_3$), 45.1 (1C, C$_1$), 24.3 (1C, C$_4$).

(3S)-3-amino-4-(1H-imidazol-4-yl)-1-[4-(phenylethynyl)phenyl] butan-2-one dihydrochlorhydrate (3a)

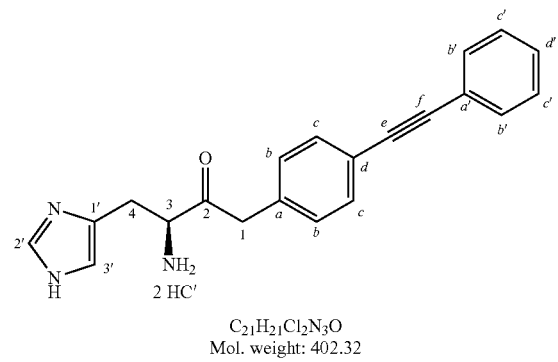

3a

C$_{21}$H$_{21}$Cl$_2$N$_3$O
Mol. weight: 402.32

M.p. 194° C. (decomposition); MS (ESI$^+$/ESI$^-$): m/z 330 (M+H)$^+$, 659 (2M+H)$^+$; 328 (M−H)$^-$, 364 (M+Cl)$^-$, 693 (2M+Cl)$^-$; $^1$H NMR (400 MHz, DMSO-d$_6$) δ: 14.69 (s, 2H, NH$_2^+$), 9.11 (d, J=1.1 Hz, 1H, H$_{2'}$), 8.63 (s, 3H, NH$_3^+$), 7.53 (m, 5H, H$_{b,c,b',c',d',3'}$), 7.43 (m, 2H, H$_{b,c,b',c',d'}$), 7.27 (m, 2H, H$_{b,c,b',c',d'}$), 4.72 (dd, J=4.2 Hz, J=8.5 Hz, 1H, H$_3$), 4.23 (s, 2H, H$_1$), 3.59 (dd, J=4.4 Hz, J=15.4 Hz, 1H, H$_4$), 3.23 (dd, J=8.9 Hz, J=15.8 Hz, 1H, H$_4$); $^{13}$C-NMR (101 MHz, DMSO-d$_6$) δ: 202.5 (1C, C$_2$), 134.2 (1C, C$_{2'}$), 134.2 (1C, C$_a$), 132.1 (1C, C$_{2'}$), 131.3 (2C, C$_{b,c,b',c',d'}$), 131.2 (2C, C$_{b,c,b',c',d'}$), 130.3 (2C, C$_{b,c,b',c',d'}$), 128.7 (2C, C$_{b,c,b',c',d'}$), 126.5 (1C, C$_{1'}$), 122.2 (1C, C$_{d,a'}$), 120.7 (1C, C$_{d,a'}$), 118.2 (1C, C$_{3'}$), 89.2 (1C, C$_{e,f}$), 89.1 (1C, C$_{e,f}$), 56.9 (1C, C$_3$), 45.1 (1C, C$_1$), 24.3 (1C, C$_4$).

(3S)-3-amino-4-(1H-imidazol-4-yl)-1-{4-[(4-methylphenyl)ethynyl]phenyl}butan-2-one dihydrochlorhydrate (3b)

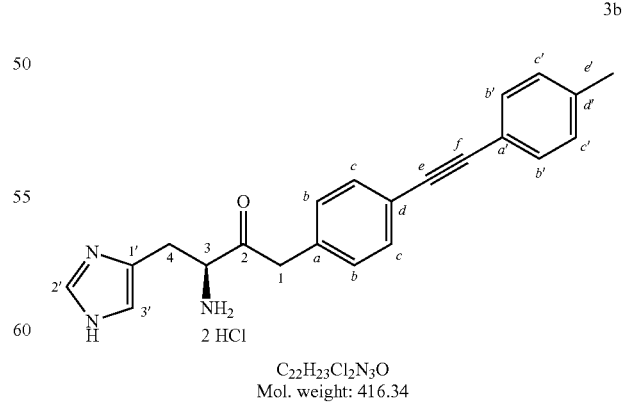

3b

C$_{22}$H$_{23}$Cl$_2$N$_3$O
Mol. weight: 416.34

M.p. 181° C. (decomposition); MS (ESI$^+$/ESI$^-$): m/z 344 (M+H)$^+$, 687 (2M+H)$^+$; 342 (M−H)$^-$, 378 (M+Cl)$^-$, 722 (2M+Cl)$^-$; $^1$HNMR (400 MHz, DMSO-d$_6$) δ (ppm): 14.53 (s, 2H, NH$_2^+$), 9.13 (s, 1H, H$_{2'}$), 8.64 (s, 3H, NH$_3^+$), 7.46 (m, 5H, $H_{b,c,b',c',d',3'}$), 7.26 (d, 4H, $H_{b,c,b',c',d'}$), 4.72 (broad s, 1H, $H_3$), 4.22 (s, 2H, $H_1$), 3.59 (dd, J=4.5 Hz, J=15.4 Hz, 1H, $H_4$), 3.23 (dd, J=8.9 Hz, J=15.7 Hz, 1H, $H_4$), 2.33 (s, 3H, $H_{e'}$); $^{13}$C-NMR (101 MHz, DMSO-$d_6$) δ (ppm): 202.6 (1C, $C_2$), 138.5 (1C, $C_{d'}$), 134.1 (1C, $C_{2'}$), 134.0 (1C, $C_a$), 131.2 (2C, $C_{b,c,b',c'}$), 131.1 (2C, $C_{b,c,b',c'}$), 130.3 (2C, $C_{b,c,b',c'}$), 129.3 (2C, $C_{b,c,b',c'}$), 126.5 (1C, $C_{1'}$), 120.9 (1C, $C_{d,a'}$), 119.2 (1C, $C_{d,a'}$), 118.3 (1C, $C_3$), 89.4 (1C, $C_{e,f}$), 88.5 (1C, $C_{e,f}$), 56.9 (1C, $C_3$), 45.1 (1C, $C_1$), 24.1 (1C, $C_4$), 20.9 (1C, $C_{e'}$).

(3S)-3-amino-1-{4-[(4-tert-butylphenyl)ethynyl]phenyl}-4-(1H-imidazol-4-yl)butan-2-one dihydrochlorhydrate (3c)

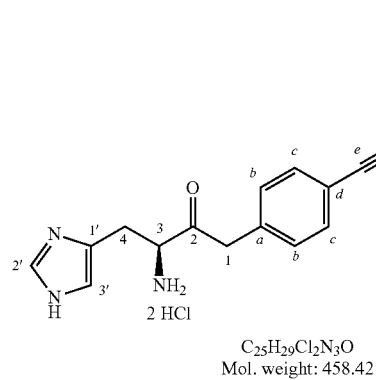

3c $C_{25}H_{29}Cl_2N_3O$
Mol. weight: 458.42

P,f, 197° C. (decomposition); MS (ESI$^+$/ESI$^-$): m/z 386 (M+H)$^+$, 771 (2M+H)$^+$; 384 (M−H)$^-$, 420 (M+Cl)$^-$, 805 (2M+Cl)$^-$; $^1$H NMR (400 MHz, DMSO-$d_6$) δ: 14.49 (s, 2H, NH$_2^+$), 9.11 (d, J=1.3 Hz, 1H, $H_{2'}$), 8.59 (s, 3H, NH$_3^+$), 7.48 (m, 7H, $H_{c,b',c',3'}$), 7.29 (d, J=8.4 Hz, 2H, $H_b$), 4.72 (dd, J=5.0 Hz, J=8.8 Hz, 1H, $H_3$), 4.21 (s, 2H, $H_1$), 3.58 (dd, J=4.5 Hz, J=15.5 Hz, 1H, $H_4$), 3.21 (dd, J=8.9 Hz, J=15.5 Hz, 1H, $H_4$), 1.29 (s, 9H, Hp); $^{13}$C-NMR (101 MHz, DMSO-$d_6$) δ: 202.5 (1C, $C_2$), 151.5 (1C, $C_{d'}$), 134.3 (1C, $C_{2'}$), 134.0 (1C, $C_a$), 131.2 (2C, $C_{c,b',c'}$), 131.0 (2C, $C_{c,b',c'}$), 130.3 (2C, $C_b$), 126.5 (1C, $C_1$), 125.5 (2C, $C_{c,b',c'}$), 120.9 (1C, $C_{d,a'}$), 119.3 (1C, $C_{d,a'}$), 118.3 (1C, $C_{3'}$), 89.4 (1C, $C_{e,f}$), 88.6 (1C, $C_{e,f}$), 56.9 (1C, $C_3$), 45.1 (1C, $C_1$), 34.5 (1C, $C_{e'}$), 30.8 (3C, $C_f$), 24.2 (1C, $C_4$).

(3S)-3-amino-4-(1H-imidazol-4-yl)-1-{4-[(4-pentylphenyl)ethynyl]phenyl}butan-2-one dihydrochlorhydrate (3d)

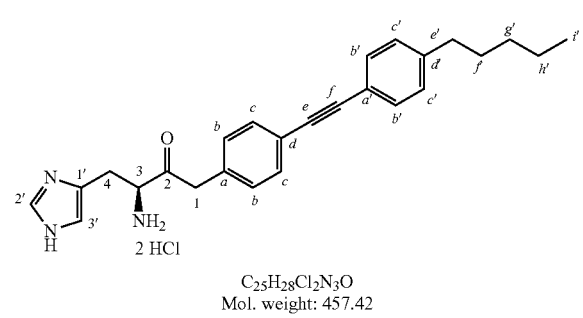

3d $C_{25}H_{28}Cl_2N_3O$
Mol. weight: 457.42

M.p. 184° C. (decomposition); MS (ESI$^+$/ESI$^-$): m/z 400 (M+H)$^+$, 799 (2M+H)$^+$; 398 (M−H)$^-$, 434 (M+Cl)$^-$, 833 (2M+Cl)$^-$; $^1$H NMR (400 MHz, DMSO-$d_6$) δ: 14.55 (s, 2H, NH$_2^+$), 9.12 (d, J=1.3 Hz, 1H, $H_{2'}$), 8.62 (s, 3H, NH$_3^+$), 7.50 (m, 5H, $H_{b,c,b',c',3'}$), 7.26 (m, 4H, $H_{b,c,b',c'}$), 4.72 (dd, J=4.3 Hz, J=8.2 Hz, 1H, $H_3$), 4.22 (s, 2H, $H_1$), 3.59 (dd, J=4.5 Hz, J=15.5 Hz, 1H, $H_4$), 3.22 (dd, 1H, J=9.0 Hz, J=15.5 Hz, $H_4$), 2.59 (t, J=7.5 Hz, 2H, $H_{e'}$), 1.57 (td, J=7.5 Hz, J=14.9 Hz, 2H, $H_f$), 1.27 (m, 4H, $H_{g',h'}$), 0.85 (t, J=7.0 Hz, 3H, $H_i$); $^{13}$C NMR (101 MHz, DMSO-$d_6$) δ: 202.5 (1C, $C_2$), 143.3 (1C, $C_{d'}$), 134.2 (1C, $C_{2'}$), 134.0 (1C, $C_a$), 131.2 (2C, $C_{b,b',c,c'}$), 131.1 (2C, $C_{b,b',c,c'}$), 130.3 (2C, $C_{b,b',c,c'}$), 128.6 (2C, $C_{b,b',c,c'}$), 126.5 (1C, $C_{1'}$), 120.9 (1C, $C_{d,a'}$), 119.4 (1C, $C_{d,a'}$), 118.3 (1C, $C_{3'}$), 89.4 (1C, $C_{e,f}$), 88.5 (1C, $C_{e,f}$), 56.9 (1C, $C_3$), 45.1 (1C, $C_1$), 34.9 (1C, $C_{e'}$), 30.759 (1C, $C_{g'}$), 30.3 (1C, $C_{f'}$), 24.1 (1C, $C_4$), 21.8 (1C, $C_{h'}$), 13.8 (1C, $C_{i'}$)

(3S)-3-amino-1-[4-(biphenyl-4-ylethynyl)phenyl]-4-(1H-imidazol-4-yl)butan-2-one dihydrochlorhydrate (3e)

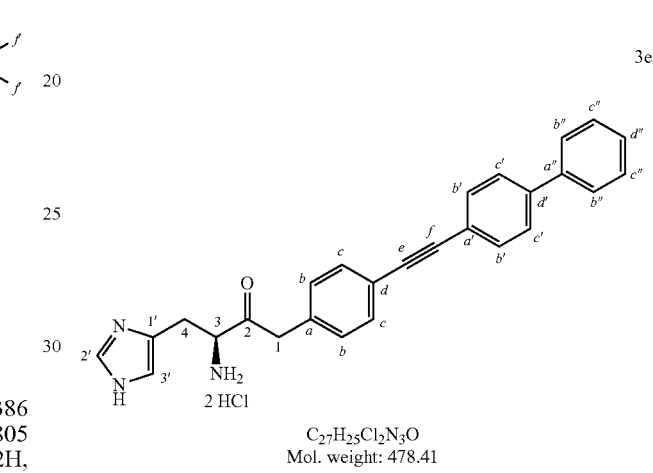

3e $C_{27}H_{25}Cl_2N_3O$
Mol. weight: 478.41

M.p. 196° C. (decomposition); MS (ESI$^+$/ESI$^-$): m/z 406 (M+H)$^+$, 811 (2M+H)$^+$; 404 (M−H)$^-$, 440 (M+Cl)$^-$, 845 (2M+Cl)$^-$; $^1$H NMR (400 MHz, DMSO-$d_6$) δ: 14.56 (s, 2H, NH$_2^+$), 9.12 (d, J=1.3 Hz, 1H, $H_{2'}$), 8.61 (s, 3H, NH$_3^+$), 7.73 (m, 4H, $H_{b,c,b',c',b'',c''}$), 7.64 (m, 2H, $H_{b,c,b',c',b'',c''}$), 7.56 (m, 2H, $H_{b,c,b',c',b'',c''}$), 7.52 (d, J=1.0 Hz, 1H, $H_{3'}$), 7.49 (m, 2H, $H_{b,c,b',c',b'',c''}$), 7.40 (m, 1H, $H_{d''}$), 7.31 (m, 2H, $H_{b,c,b',c',b'',c''}$), 4.73 (dd, J=4.3 Hz, J=8.3 Hz, 1H, $H_3$), 4.23 (s, 2H, $H_1$), 3.60 (dd, J=4.3 Hz, J=15.7 Hz, 1H, $H_4$), 3.22 (dd, J=8.9 Hz, J=15.6 Hz, 1H, $H_4$); $^{13}$C NMR (101 MHz, DMSO-$d_6$) δ: 202.5 (1C, $C_2$), 140.2 (1C, $C_{d',a''}$), 139.0 (1C, $C_{d',a''}$), 134.2 (1C, Ca), 134.2 (1C, $C_{2'}$), 131.9 (2C, $C_{b,c,b',c',b'',c''}$), 131.2 (2C, $C_{b,c,b',c',b'',c''}$), 130.3 (2C, C, $C_{b,c,b',c',b'',c''}$), 127.9 (1C, $C_{d''}$), 126.9 (2C, $C_{b,c,b',c',b'',c''}$), 126.6 (2C, $C_{b,c,b',c',b'',c''}$), 126.5 (1C, $C_{1'}$), 121.2 (1C, $C_{d,a'}$), 120.7 (1C, $C_{d,a'}$), 118.3 (1C, $C_{3'}$), 89.9 (1C, $C_{e,f}$), 89.2 (1C, $C_{e,f}$), 57.0 (1C, $C_3$), 45.1 (1C, $C_1$), 24.2 (1C, $C_4$)

Example 4

Measurement of the Inhibitory Effect of the Different Compounds of the Invention on Purified *B. suis* histidinol dehydrogenase.

The activity of HDH vis-à-vis the different compounds was measured by monitoring the reduction of $NAD^+$ to NADH directly at 340 nm ($\epsilon_M$=6200 $M^{-1}cm^{-1}$) as described in the prior art (Loper, J. C.; Adams, E. *J. Biol. Chem.* 240 (1965): 788-795). The enzymatic activity was studied at 30° C. in the presence of 0.5 mM of histidinol, 5 mM of $NAD^+$ and 0.5 mM of $MnCl_2$ in a 50 mM sodium glycinate buffer, pH=9.2.

For the kinetic studies, the experiments were carried out with 150 mM sodium glycinate (pH=9.2) and 2 mM $NAD^+$.

The $K_m$ for the substrate was determined by varying the concentration of the histidinol from 10 to 50 µM. The activity (1U) is defined as the quantity of HDH producing 1 µM of NADH per minute in the reaction.

In order to determine the $IC_{50}$ of the different inhibitors, the latter were added at different concentrations ranging from 1 to 200 nM and pre-incubated with the enzyme solution at 30° C. for 5 minutes before initiation of the reaction.

The enzyme concentration in the system is 4. $10^{-11}$ M.

The results obtained ($IC_{50}$) for the different inhibitors are presented in Table 1 below:

TABLE 1

$IC_{50}$ of the different compounds vis-à-vis the catalytic activity of *B. suis* histidinol dehydrogenase (nd = not determined)

| Compounds | *B. suis* HDH $IC_{50}$ (nM) |
|---|---|
| 2a | 30 |
| 2b | 40 |
| 2c | 20 |
| 2d | 30 |
| 2e | nd |
| 2f | 70 |
| 2g | nd |
| 2h | 30 |
| 2i | 13 |
| 2j | 25 |
| 2k | 40 |
| 2l | 65 |
| 2m | 30 |
| 2n | nd |
| 3a | 3 |
| 3b | 40 |
| 3c | 65 |
| 3d | 8.5 |
| 3e | nd |

Table 1 shows that all the tested compounds of the invention have a high affinity for HDH ($IC_{50}$ comprised between 70 and 3 nM).

Compound 3a possesses a significant affinity for HDH.

Compared with the compounds published in Abdo et al. [Abdo et al. *Bioorg. Med. Chem.* 15 (2007): 4427-4433], the compounds according to the invention exhibit a comparable inhibitory activity of nanomolar order on the purified HDH.

Similar results are obtained on the HDH of *Mycobacterium.*

Example 5

Effects of the *B. suis* HDH Inhibitors on the Growth of *B. suis* in Minimal Medium A stationary phase culture of *B. suis* is carried out over 24 h in TS (tryptic soya) broth starting from a streak of the bacterium on agar. The bacterial pellet is recovered by centrifugation, then washed (PBS) and resuspended in minimal medium [Gerhardt et al., *J Bacteriol* 59 (1950): 777-782] in the volume of the original culture. 30 microlitres of this bacterial suspension are used for seeding 3 ml of minimal medium. Typically, the inhibitors to be studied are then added at concentrations of 10, 50 or 100 micromolar. A control culture contains no inhibitor.

The cultures are stirred at 37° C. and the growth is monitored by OD measurement (600 nm) at 48, 72 and 96 h.

The results corresponding to the percentage of inhibition of the bacterial growth in minimal medium are presented in Table 2 below:

TABLE 2 inhibition of bacterial growth in liquid medium of *B. suis* bacteria in the presence of 100 µM or 50 µM.

| Compounds | Inhibition of *B. suis* HDH $IC_{50}$ (nM) | Effects on the growth of *B. suis* (%) 7 days in minimal medium 100 µM | 50 µM |
|---|---|---|---|
| 2a | 30 | 40 | 30 |
| 2b | 40 | 60 | 50 |
| 2c | 20 | 60 | 30 |
| 2d | 30 | 90 | 70 |
| 2f | 70 | 90 | 70 |
| 2h | 30 | 100 | 100 |
| 2k | 40 | 100 | 100 |
| 3a | 3 | 100 | 100 |
| 3c | 65 | 30 | 30 |
| 3d | 8.5 | 30 | 30 |

The results indicate that the compounds 2h, 2k and particularly 3a completely inhibit the growth of the bacteria in liquid medium, starting from a concentration of 50 nM.

These results also show that the inhibitors are capable of reaching their target in the intact and live pathogen, thus confirming their ability to cross the prokaryotic membranes.

Example 6

Effects of the *B. suis* HDH Inhibitors on the Growth of *B. suis* in the Macrophage The differentiated cells of the transformed human macrophage line THP-1 are seeded at a concentration of 500,000 cell./ml/well in 24-well plates and incubated for 24 h at 37° C./5% $CO_2$ in RPMI medium/10% FCS. The infection of the cells is carried out at a multiplicity of infection (MOI) of 20. For this, the appropriate quantity of a stationary culture of *B. suis* ($10^{10}$ bacteria/ml) is taken up in 100 microlitres of RPMI per well of cells and added to the THP-1 cells. After incubation for 45 minutes, the cells are washed twice with PBS and incubated with 1 ml of RPMI/10% FCS per well containing gentamicin (30 micrograms/ml). After incubation for 1 hour, the cells in the first series of wells are washed once with PBS, lysed with triton X-100 (0.2%) and spread on TS agar. The number of intracellular bacteria is counted after incubation for 3 days at 37° C. The remaining wells are divided into untreated wells (control) and wells treated with the inhibitor of interest (typically at 10 and 25 nM in RPMI). The lyses and spreading operations (see above) are carried out 4 h, 7 h and 24 h after the infection. The experiments are carried out in triplicate.

The results for the proliferation of intracellular *B. suis* treated with compound 3a are presented in FIG. 1.

The experimental results show that compound 3a is capable of penetrating into THP-1 cells infected with *B. suis*. Also, the results show that compound 3a effectively inhibits (approximately 1000 times) the intracellular proliferation of the bacteria when they are in the macrophage. This compound is therefore active not only on isolated bacteria in minimal medium, but also on the pathogen in the intracellular state. The inhibitor will therefore subsequently facilitate the elimination of the pathogen by the immune system of the host.

The invention claimed is:

1. Compounds of general formula (I) below:

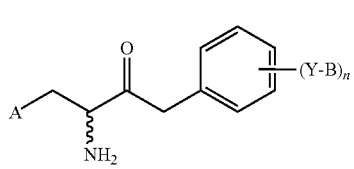
(I)

wherein
A represents a $C_5$-$C_{10}$ heterocyclic group, comprising 1 to 6 heteroatoms chosen from the elements of the chalcogen and pnictogen families, and
the phenyl group is substituted by n Y—B group(s), n varying from 1 to 5, said Y—B group being such that:
Y represents a single bond or a saturated or unsaturated, linear or branched alkylene group, comprising from 1 to 6 carbon atoms, and
B represents a group selected from the group consisting of:
an aryl or heteroaryl group,
an A group as defined above, and
a $C_3$-$C_6$ cycloalkyl group,
said B group being substituted by one or more substituent(s), said substituent(s) being selected from the group consisting of:
a halogen atom,
an alkoxy group comprising from 1 to 4 carbon atoms,
an aryloxy group,
a saturated or unsaturated, linear, branched or cyclic alkyl group, comprising from 1 to 6 carbon atoms, optionally substituted by one or more halogen atoms, and
an aryl group, optionally substituted by a $C_1$-$C_4$ alkyl,
a hydroxyl group,
a thiol group,
an amine group,
an amide group,
a carboxylic acid group,
a cyano group,
an azide group, and
a nitro group,
said compounds being in a form selected from the group consisting of a racemate, an enantiomer, a tautomer corresponding to a racemate, and a tautomer corresponding to an enantiomer, and pharmaceutically acceptable salts thereof.

2. The compounds according to claim 1, wherein the compounds are of general formula (Ia) below:

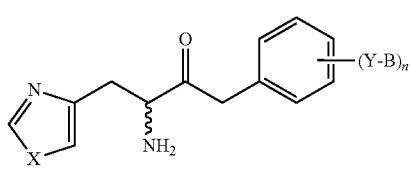
(Ia)

where X is a heteroatom chosen from the elements of the chalcogen or pnictogen family.

3. The compounds according to claim 1, wherein the compounds are of general formula (Ia), where X represents N.

4. The compounds according to claim 1, wherein the compounds are of general formula (Ib) below:

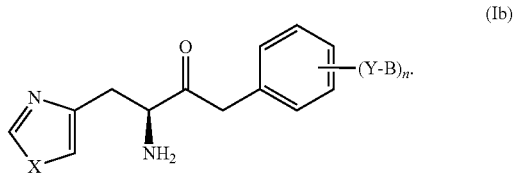
(Ib)

5. The compounds according to claim 3, wherein said compounds are monosubstituted by the Y—B group, said Y—B group being such that:
Y represents a single bond, a $C_1$-$C_3$ alkylene, a $C_2$-$C_3$ alkenylene or a $C_2$-$C_3$ alkynylene, and
B represents an aryl or heteroaryl group, substituted by:
a halogen atom,
an alkoxy group comprising from 1 to 4 carbon atoms,
an aryloxy group,
a saturated or unsaturated, linear, branched or cyclic alkyl group, comprising from 1 to 6 carbon atoms, optionally substituted by one or more halogen atoms, and
an aryl group, optionally substituted by a $C_1$-$C_4$ alkyl,
a hydroxyl group,
a thiol group,
a primary, secondary or ternary amine group
an amide group,
a carboxylic acid group,
a cyano group,
an azide group, and
a nitro group.

6. The compounds according to claim 3, wherein Y—B is in the para position of the phenyl group.

7. The compounds according to claim 1, said compounds being being selected from the group consisting of:

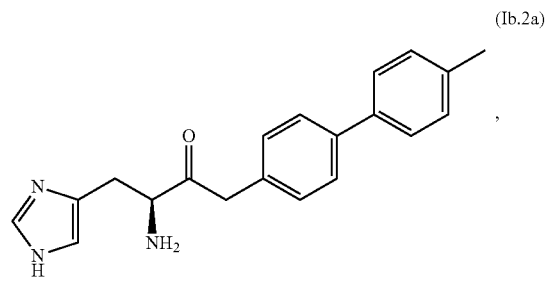
(Ib.2a)

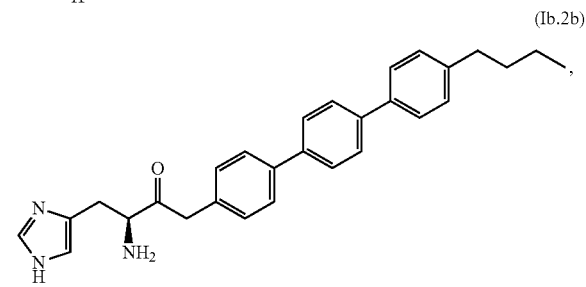
(Ib.2b)

(Ib.2c)
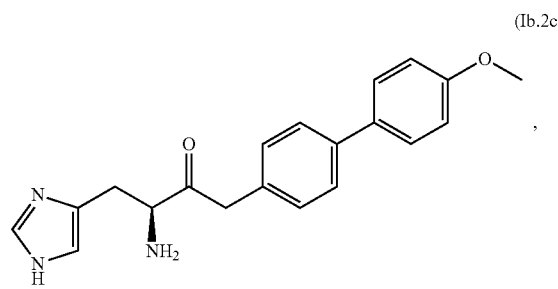
(Ib.2d)
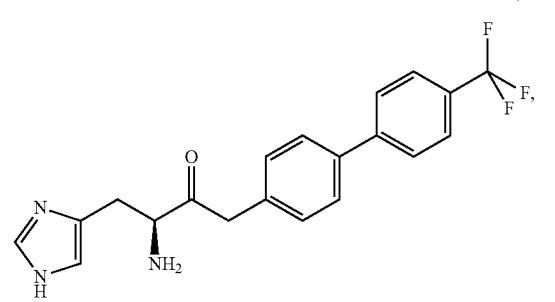
(Ib.2e)
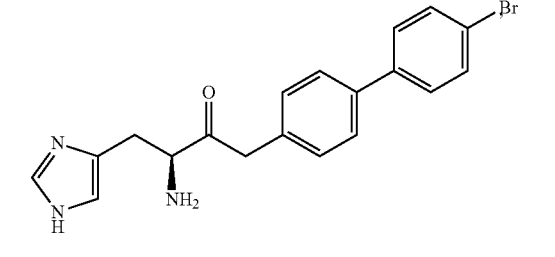
(Ib.2f)
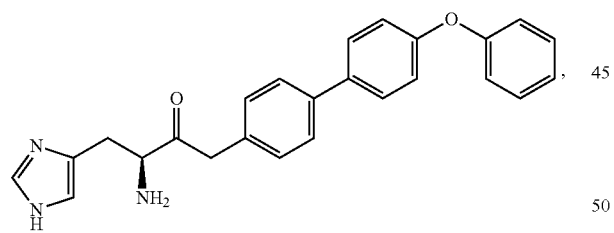
(Ib.2g)
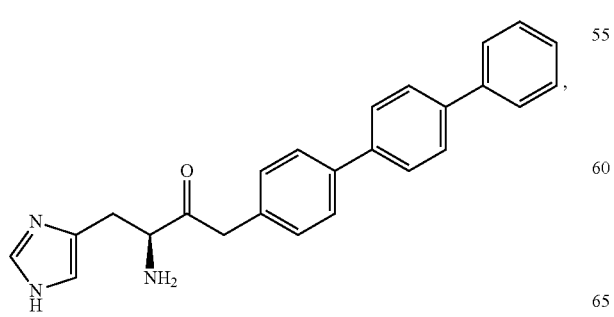
(Ib.2h)
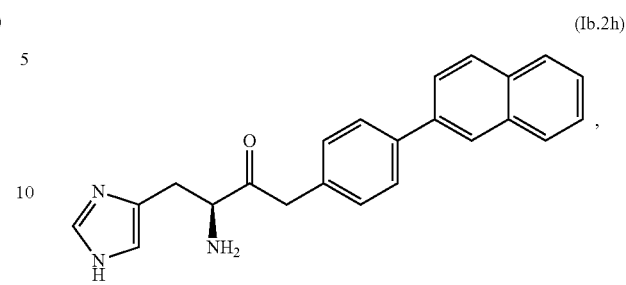
(Ib.2i)
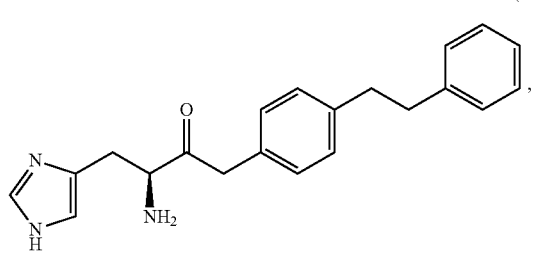
(Ib.2j)
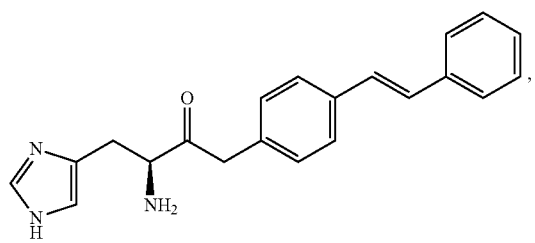
(Ib.2k)
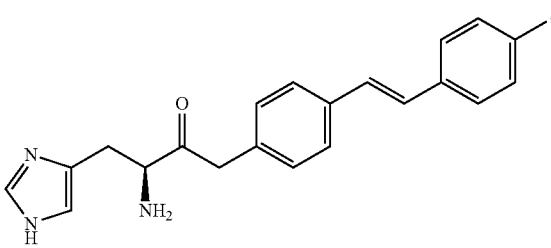
(Ib.2l)
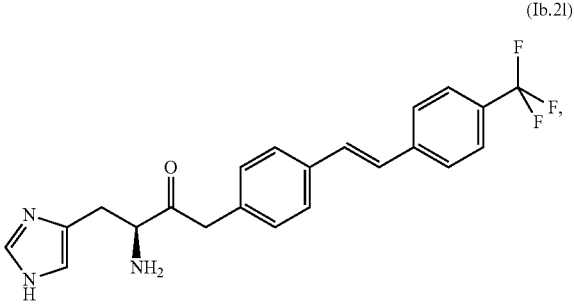

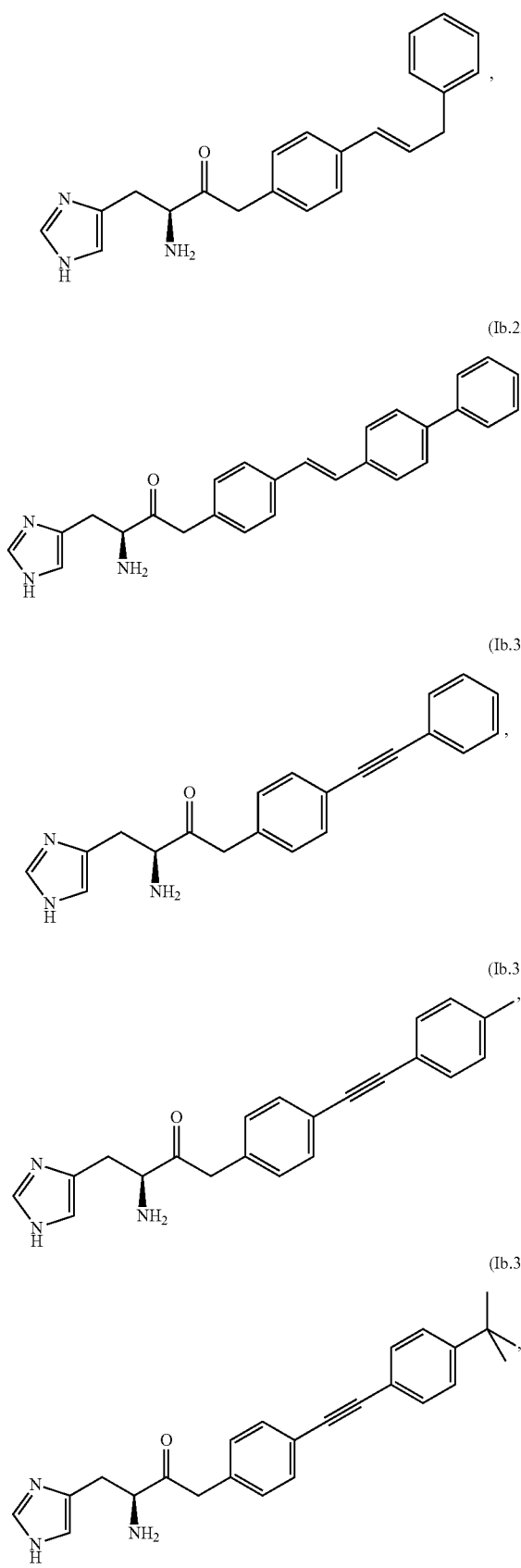
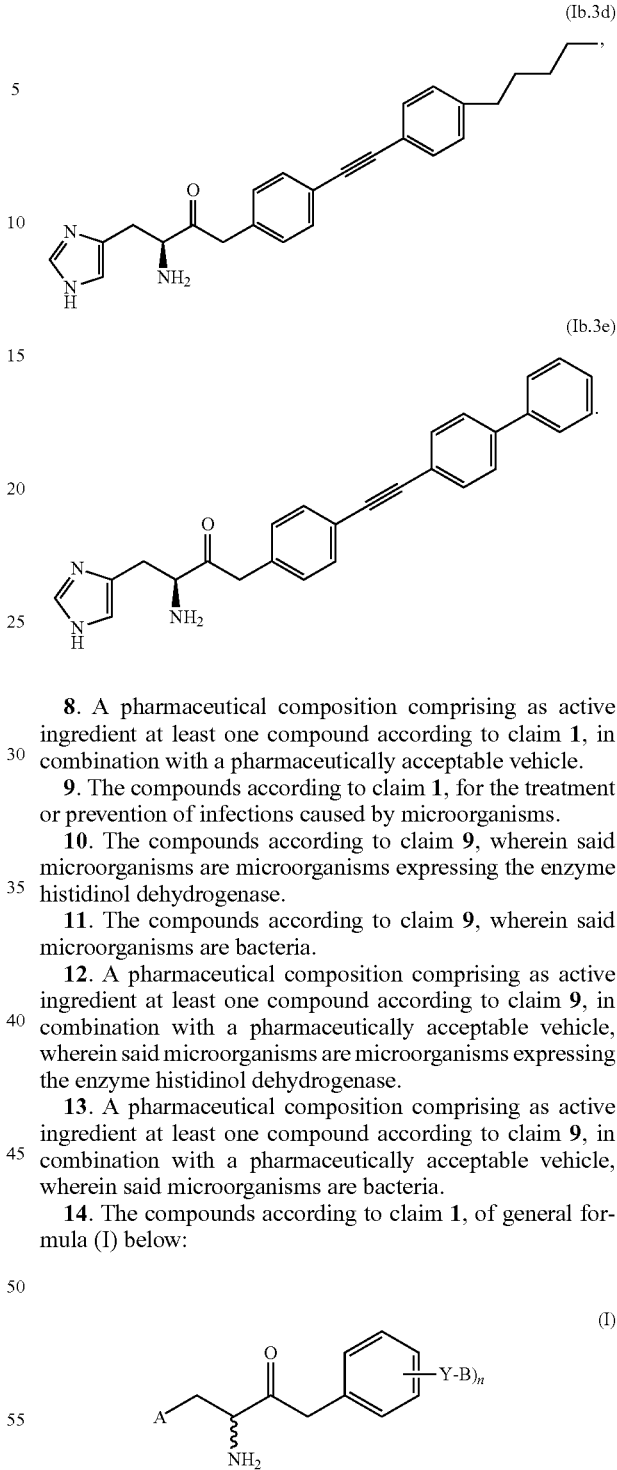

8. A pharmaceutical composition comprising as active ingredient at least one compound according to claim 1, in combination with a pharmaceutically acceptable vehicle.

9. The compounds according to claim 1, for the treatment or prevention of infections caused by microorganisms.

10. The compounds according to claim 9, wherein said microorganisms are microorganisms expressing the enzyme histidinol dehydrogenase.

11. The compounds according to claim 9, wherein said microorganisms are bacteria.

12. A pharmaceutical composition comprising as active ingredient at least one compound according to claim 9, in combination with a pharmaceutically acceptable vehicle, wherein said microorganisms are microorganisms expressing the enzyme histidinol dehydrogenase.

13. A pharmaceutical composition comprising as active ingredient at least one compound according to claim 9, in combination with a pharmaceutically acceptable vehicle, wherein said microorganisms are bacteria.

14. The compounds according to claim 1, of general formula (I) below:

wherein:
A represents a $C_5$-$C_6$ heterocyclic group, comprising 1 to 6 heteroatoms chosen from the elements of the chalcogen and pnictogen families, and
the phenyl group is substituted by n Y—B group(s), n varying from 1 to 5, said Y—B group being such that:
Y represents a single bond or a saturated or unsaturated, linear or branched alkylene group, comprising from 2 to 4 carbon atoms, and B represents a group selected from the group consisting of:
- a phenyl or naphthyl group
- an A group as defined above, and
- a $C_3$-$C_6$ cycloalkyl group, said B group being substituted by one substituent, said substituent(s) being selected from the group consisting of:
- a halogen atom,
- an alkoxy group comprising from 1 to 4 carbon atoms,
- a phenyloxy group,
- a saturated or unsaturated, linear, branched or cyclic alkyl group, comprising from 2 to 4 carbon atoms, optionally substituted by one or more halogen atoms, and
- a phenyl group, optionally substituted by a $C_1$-$C_4$ alkyl,
- a hydroxyl group,
- a thiol group,
- an amine group,
- an amide group,
- a carboxylic acid group,
- a cyano group,
- an azide group, and
- a nitro group, said compounds being in the form selected from the group consisting of an enantiomer, a tautomer corresponding to a racemate, and a tautomer corresponding to an enantiomer, and pharmaceutically acceptable salts thereof.

15. The compounds according to claim 5, wherein said compounds are monosubstituted by the Y—B group, said Y—B group being such that:

Y represents a single bond, a $C_1$-$C_3$ alkylene, a $C_2$-$C_3$ alkenylene or a $C_2$-$C_3$ alkynylene, and B represents a phenyl group, substituted by an atom or group selected from the group consisting of:
- a halogen atom,
- an alkoxy group comprising from 1 to 4 carbon atoms,
- a phenyloxy group,
- a saturated or unsaturated, linear, branched or cyclic alkyl group, comprising from 2 to 4 carbon atoms, optionally substituted by one or more halogen atoms, and
- a phenyl group, optionally substituted by a $C_1$-$C_4$ alkyl,
- a hydroxyl group,
- a thiol group,
- a primary, secondary or ternary amine group
- an amide group,
- a carboxylic acid group,
- a cyano group,
- an azide group, and
- a nitro group.

* * * * *